US008470552B2

(12) United States Patent
Croughan et al.

(10) Patent No.: US 8,470,552 B2
(45) Date of Patent: Jun. 25, 2013

(54) STRATEGY TO REDUCE LACTIC ACID PRODUCTION AND CONTROL PH IN ANIMAL CELL CULTURE

(75) Inventors: Matthew S. Croughan, Claremont, CA (US); Nathaniel W. Freund, Camarillo, CA (US)

(73) Assignee: Keck Graduate Institute, Claremont, CA (US)

( * ) Notice: Subject to any disclaimer, the term of this patent is extended or adjusted under 35 U.S.C. 154(b) by 18 days.

(21) Appl. No.: 12/903,046

(22) Filed: Oct. 12, 2010

(65) Prior Publication Data

US 2011/0104734 A1 May 5, 2011

Related U.S. Application Data

(60) Provisional application No. 61/250,798, filed on Oct. 12, 2009.

(51) Int. Cl.
*C12P 21/06* (2006.01)
*C12N 5/00* (2006.01)
*C12N 5/02* (2006.01)
*C12N 15/63* (2006.01)
*C12N 15/85* (2006.01)

(52) U.S. Cl.
USPC .......................... 435/69.1; 435/375; 435/455

(58) Field of Classification Search
USPC ........................................ 435/69.1, 375, 455
See application file for complete search history.

(56) References Cited

U.S. PATENT DOCUMENTS

| | | | |
|---|---|---|---|
| 5,641,870 A | 6/1997 | Rinderknecht et al. | 530/417 |
| 7,335,491 B2 | 2/2008 | Drapeau et al. | 435/69.1 |

OTHER PUBLICATIONS

Cruz et al., 2000, Enzyme and Microbial Technology, vol. 27, p. 43-52.*
Altamirano et al., "Decoupling Cell Growth and Product Formation in Chinese Hamster Ovary Cells Through Metabolic Control," *Biotechnology and Bioengineering*, 76(4):351-360, 2001.
Altamirano et al., "Improvement of CHO Cell Culture Medium Formulation: Simultaneous Substitution of Glucose and Glutamine," *Biotechnol. Prog.*, 16(1):69-75, 2000.
Chen et al., "Engineering of a Mammalian Cell Line for Reduction of Lactate Formation and High Monoclonal Antibody Production," *Biotechnology and Bioengineering*, 72(1):55-61, 2001.
Chu et al., "Industrial choices for protein production by large-scale cell culture," *Current Opinion in Biotechnology*, 12:180-187, 2001.
Dorai et al., "Expression of Anti-Apoptosis Genes Alters Lactate Metabolism of Chinese Hamster Ovary Cells in Culture," *Biotechnology and Bioengineering*, 103(3):592-608, 2009.
Duval et al., "Role of Metabolic Waste Products in the Control of Cell Proliferation and Antibody Production by Mouse Hybridoma Cells," *Hybridoma* 11(3):311-322, 1992.
Glacken, "Catabolic Control of Mammalian Cell Culture," *Bio/Technology*, 6:1041-1050, 1988.
Gódia et al., Ozturk et al. (eds.), *Cell Culture Technology for Pharmaceutical and Cell-Based Therapies*, Taylor & Francis Group, LLC, New York, London, 2006, Chap. 4, "Cell Metabolism," pp. 81-112.

Irani et al., "Improvement of the Primary Metabolism of Cell Cultures by Introducing a New Cytoplasmic Pyruvate Carboxylase Reaction," *Biotechnology and Bioengineering*, 66(4):238-246, 1999.
Jeong et al., "Blocking of Acidosis-Mediated Apoptosis by a Reduction of Lactate Dehydrogenase Activity through Antisense mRNA Expression," *Biochemical and Biophysical Research Communications*, 289(5):1141-1149, 2001.
Kim et al., "Down-regulation of lactate dehydrogenase-A by siRNAs for reduced lactic acid formation of Chinese hamster ovary cells producing thrombopoietin," *Applied Microbiol. Biotechnol.*, 74:152-159, 2007.
Kim et al., "Functional expression of human pyruvate carboxylase for reduced lactic acid formation of Chinese hamster ovary cells (DG44)," *Appl. Microbiol. Biotechnol.*, 76:659-665, 2007.
Lao et al., "Effects of Ammonium and Lactate on Growth and Metabolism of a Recombinant Chinese Hamster Ovary Cell Culture," *Biotechnol. Prog.*, 13(5):688-691, 1997.
Lehninger, "The Standard Free-Energy Change is Directly Related to the Equilibrium Constant," *Principles of Biochemistry*, Part III: Bioenergetics and Metabolism, pp. 494, 497, 542, 543, and 633, 2000.
Maranga et al., "Metabolism of PER.C6™ Cells Cultivated Under Fed-Batch Conditions at Low Glucose and Glutamine Levels," *Biotechnology and Bioengineering*, 94(1):139-150, 2006.
McQueen et al., "Effect of Ammonium Ion and Extracellular pH on Hybridoma Cell Metabolism and Antibody Production," *Biotechnology and Bioengineering*, 35:1067-1077, 1990.
Meier, "Cell culture scale-up: mixing, mass transfer, and use of appropriate scale-down models," *Biochemical engineering XIV*, 2005, abstract only.
Nyberg et al., "Metabolic Effects on Recombinant Interferon-γ Glycosylation in Continuous Culture of Chinese Hamster Ovary Cells," *Biotechnology and Bioengineering*, 62(3):336-347, 1999.
Omasa et al., "Effects of Lactate Concentration on Hybridoma Culture in Lactate-Controlled Fed-Batch Operation," *Biotechnology and Bioengineering*, 39(5):556-564, 1992.
Ozturk et al., "Effects of Ammonia and Lactate on Hybridoma Growth, Metabolism, and Antibody Production," *Biotechnology and Bioengineering*, 39(4):418-431, 1992.
Paredes et al., "Modification of glucose and glutamine metabolism in hybridoma cells through metabolic engineering," *Cytotechnology*, 30:85-93, 1999.
Sinacore et al., "CHO DUKX Cell Lineages Preadapted to Growth in Serum-Free Suspension Culture Enable Rapid Development of Cell Culture Processes for the Manufacture of Recombinant Proteins," *Biotechnology and Bioengineering*, 52(4):518-528, 1996.
Xie et al., "Applications of improved stoichiometric model in medium design and fed-batch cultivation of animal cells in bioreactor," *Cystotechnology*, 15:17-29, 1994.
Yang et al., "Effects of Ammonia on CHO Cell growth, Erythropoietin Production, and Glycosylation," *Biotechnology and Bioengineering*, 68(4):370-380, 2000.
Yeo et al., "Glutamine or glucose starvation in hybridoma cultures induces death receptor and mitochondrial apoptotic pathways," *Biotechnol. Lett.*, 28:1445-1452, 2006.
Zapata et al., "Engineering linear F(ab')$_2$ fragments for efficient production in *Escherichia coli* and enhanced antiproliferative activity," *Protein Engineering*, 8(10)1057-1062, 1995.
Zhou et al., "High Viable Cell Concentration Fed-Batch Cultures of Hybridoma Cells Through On-Line Nutrient Feeding," *Biotechnology and Bioengineering*, 46(6):579-587, 1995.

* cited by examiner

*Primary Examiner* — Shin-Lin Chen
(74) *Attorney, Agent, or Firm* — Seed IP Law Group PLLC

(57) ABSTRACT

The present disclosure provides a method for culturing cells in exogenous lactic acid. Certain aspects of the present disclosure include the production of recombinant proteins, such as antibodies and fragments thereof. Certain aspects of the present disclosure also relate to methods of controlling lactic acid production, pH stability and osmolality in cell culture.

16 Claims, 22 Drawing Sheet

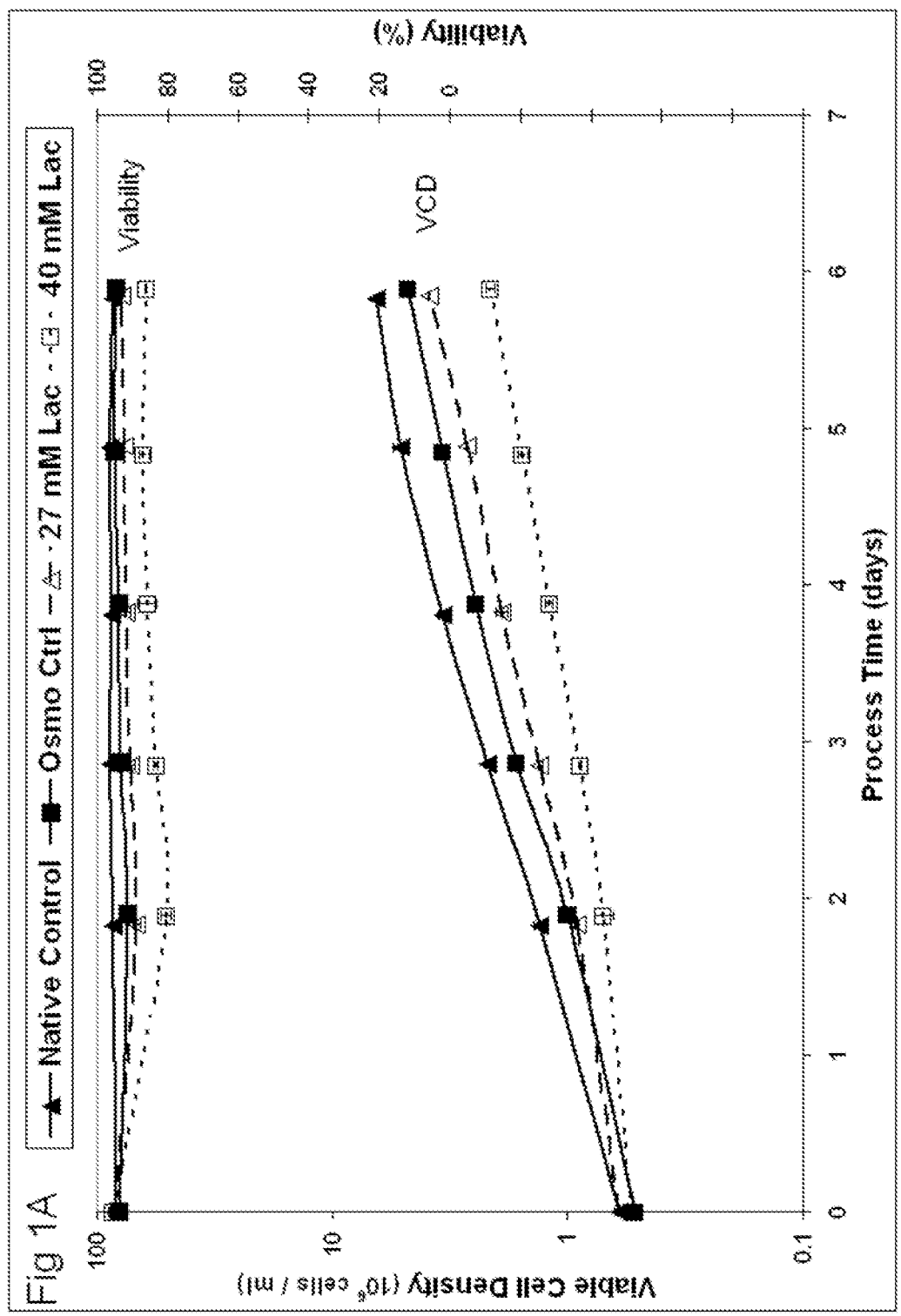

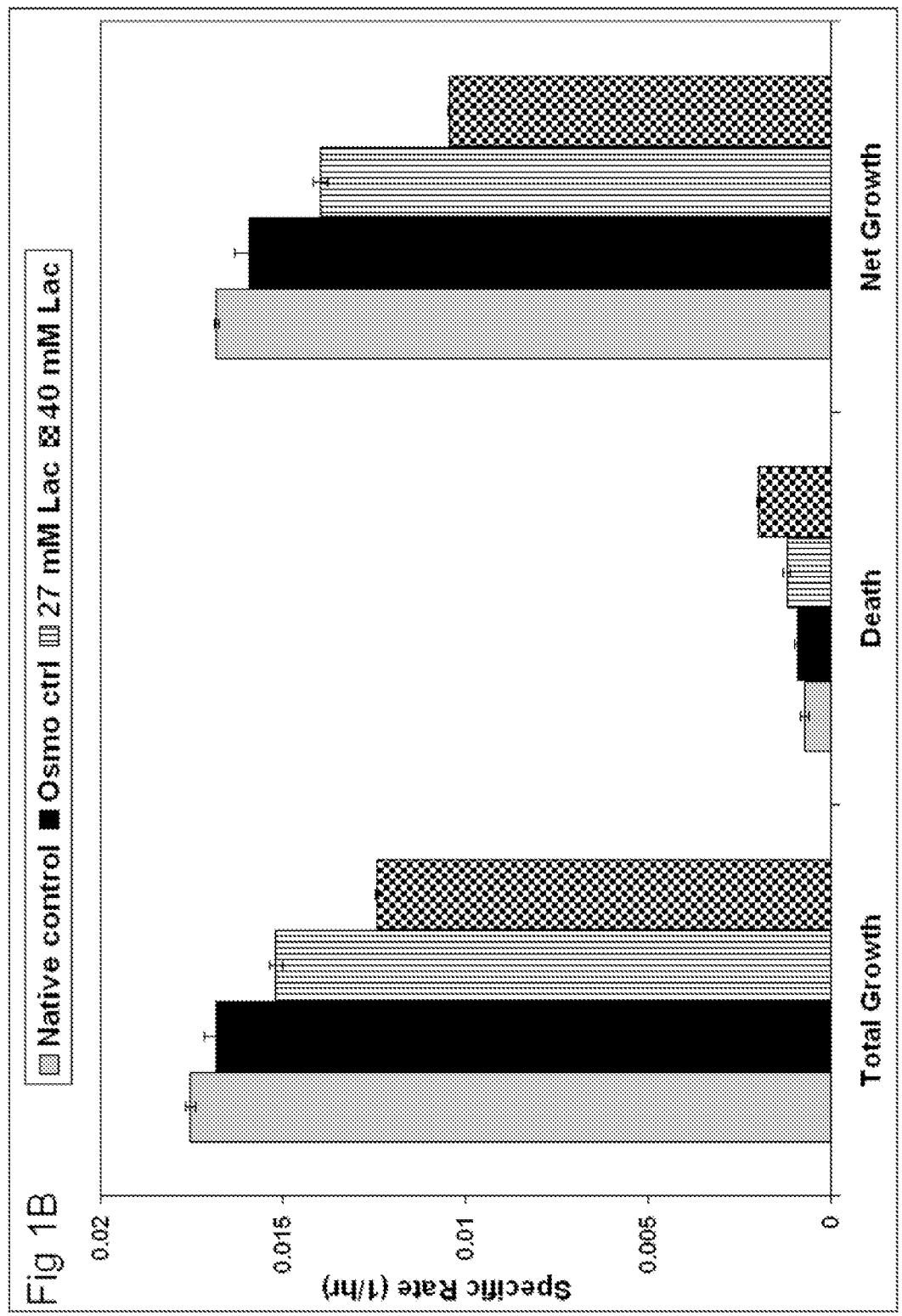

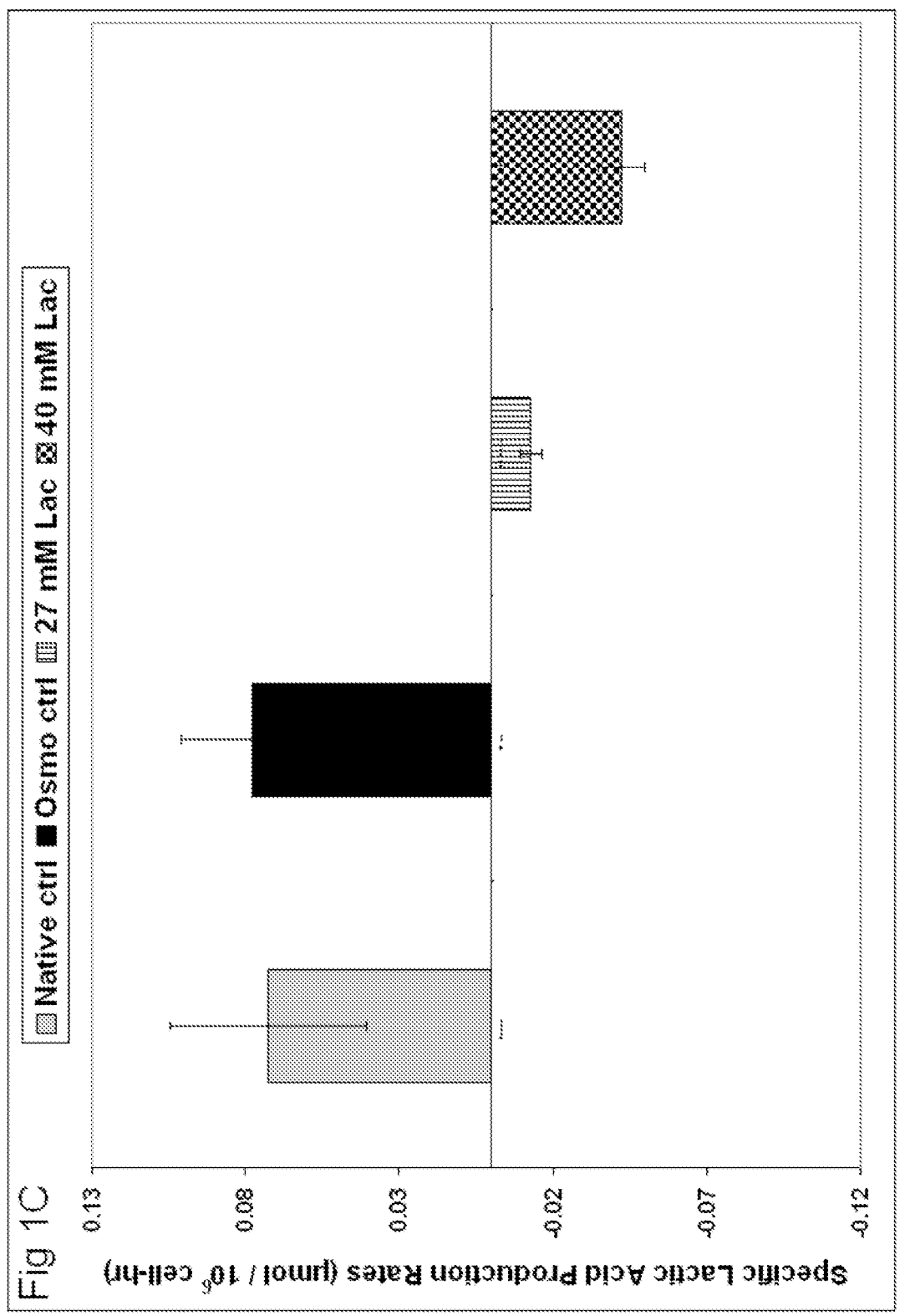

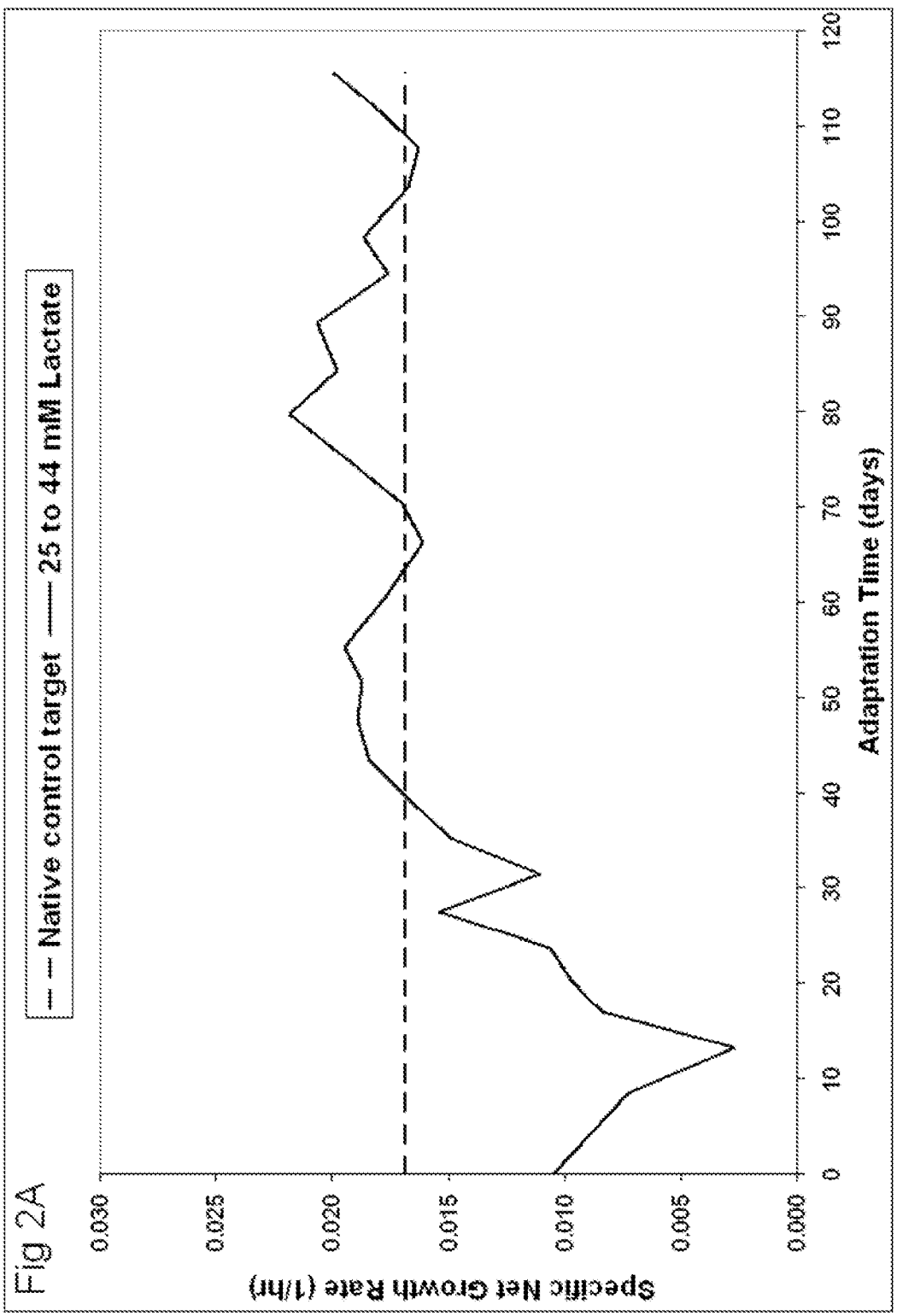

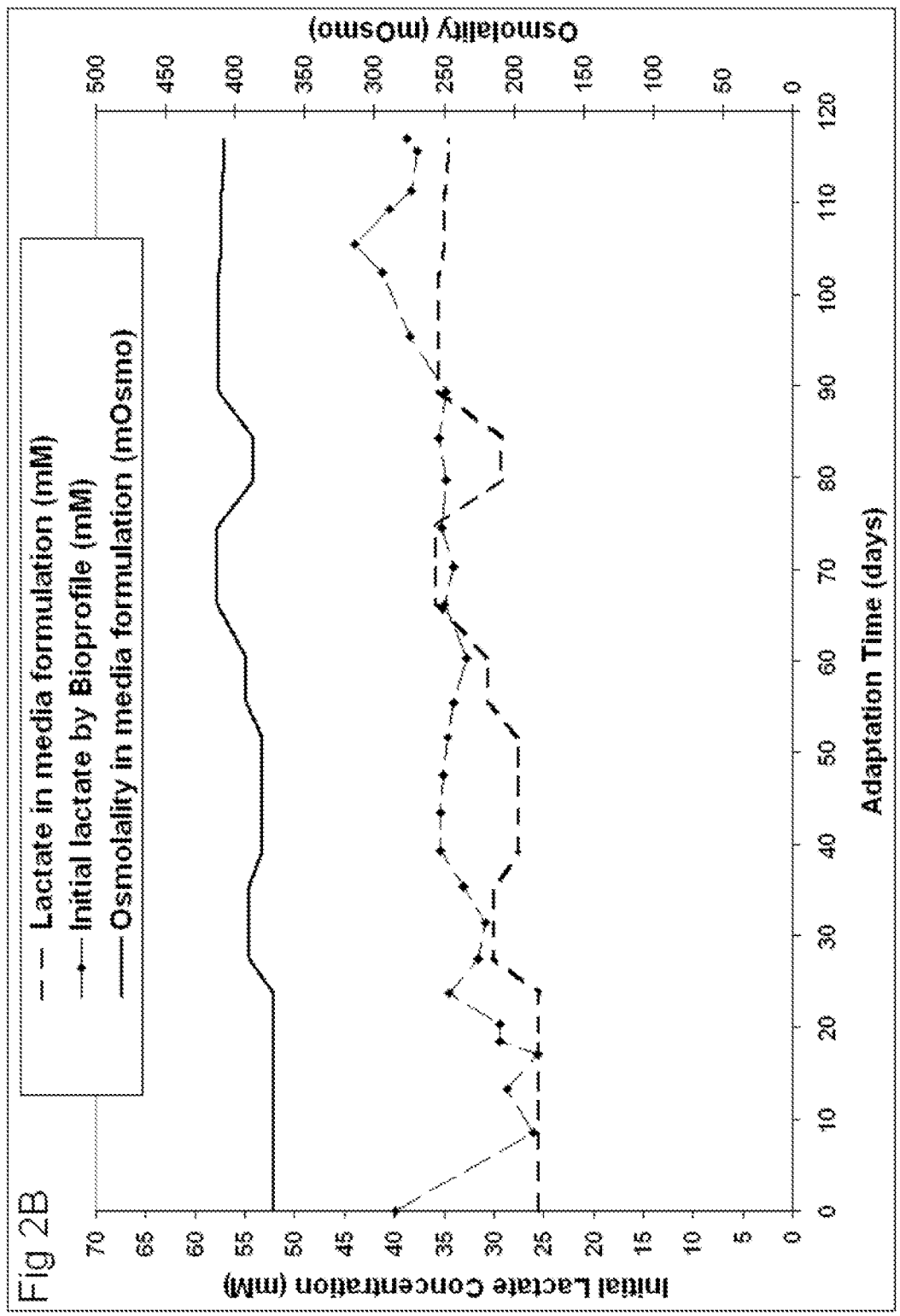

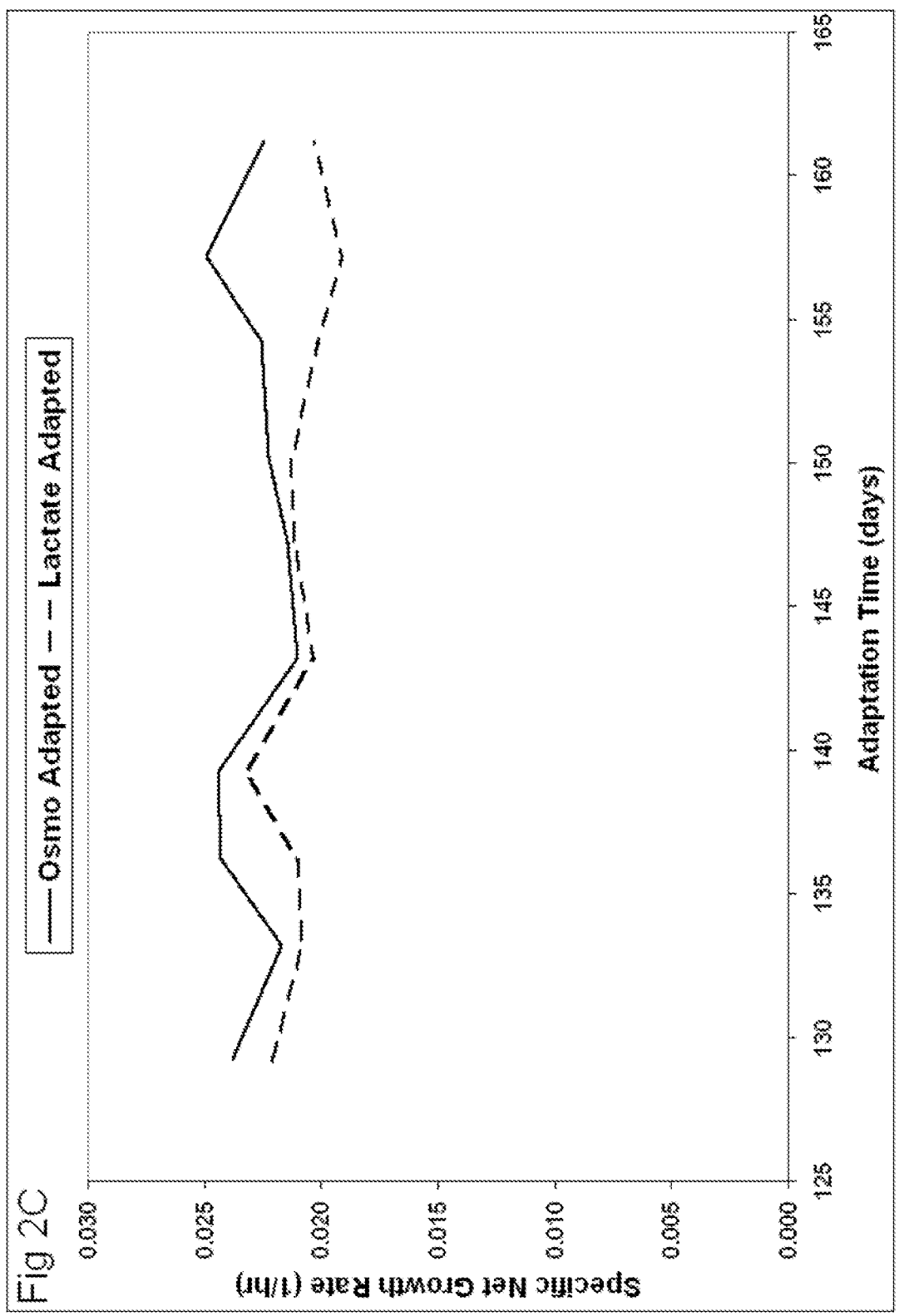

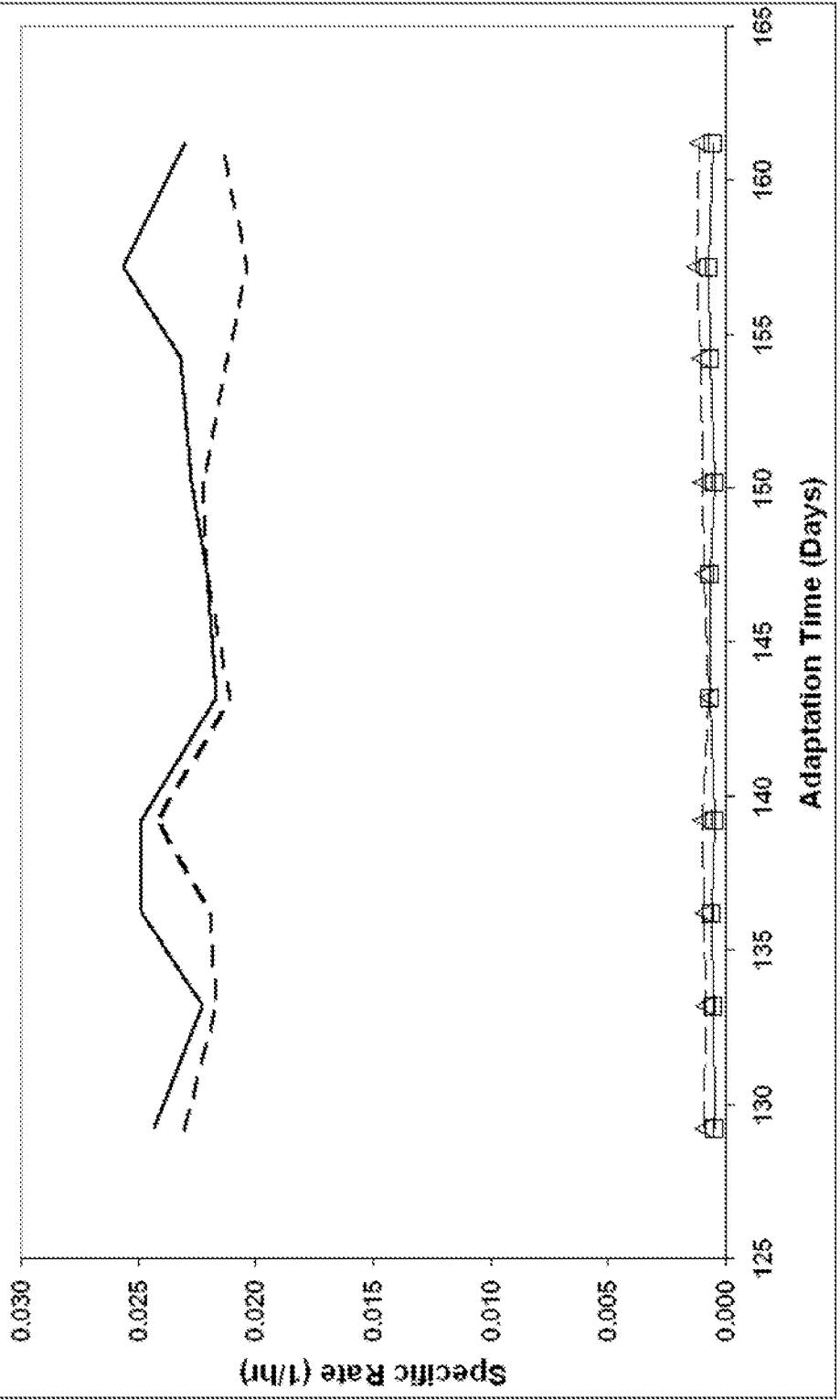

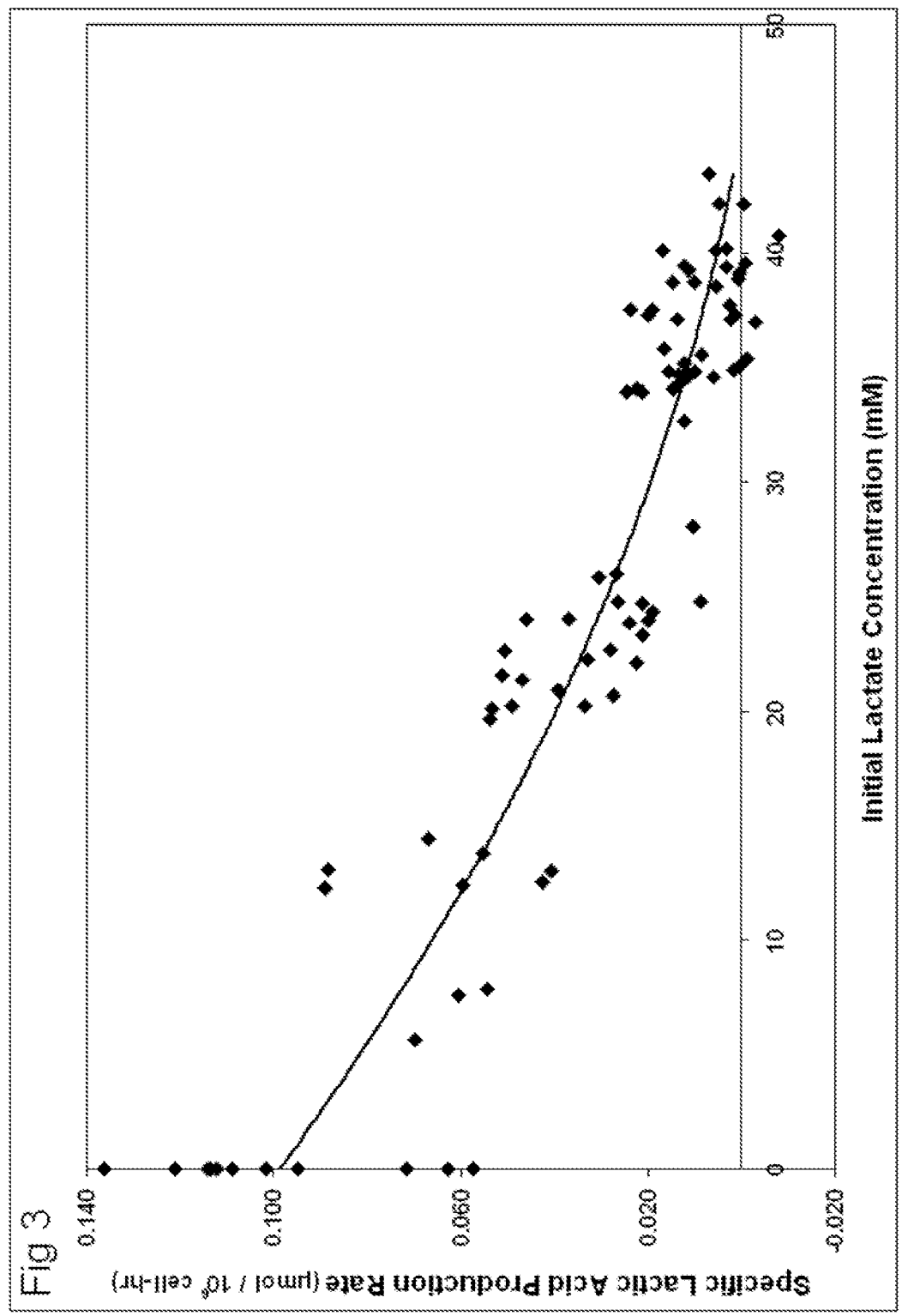

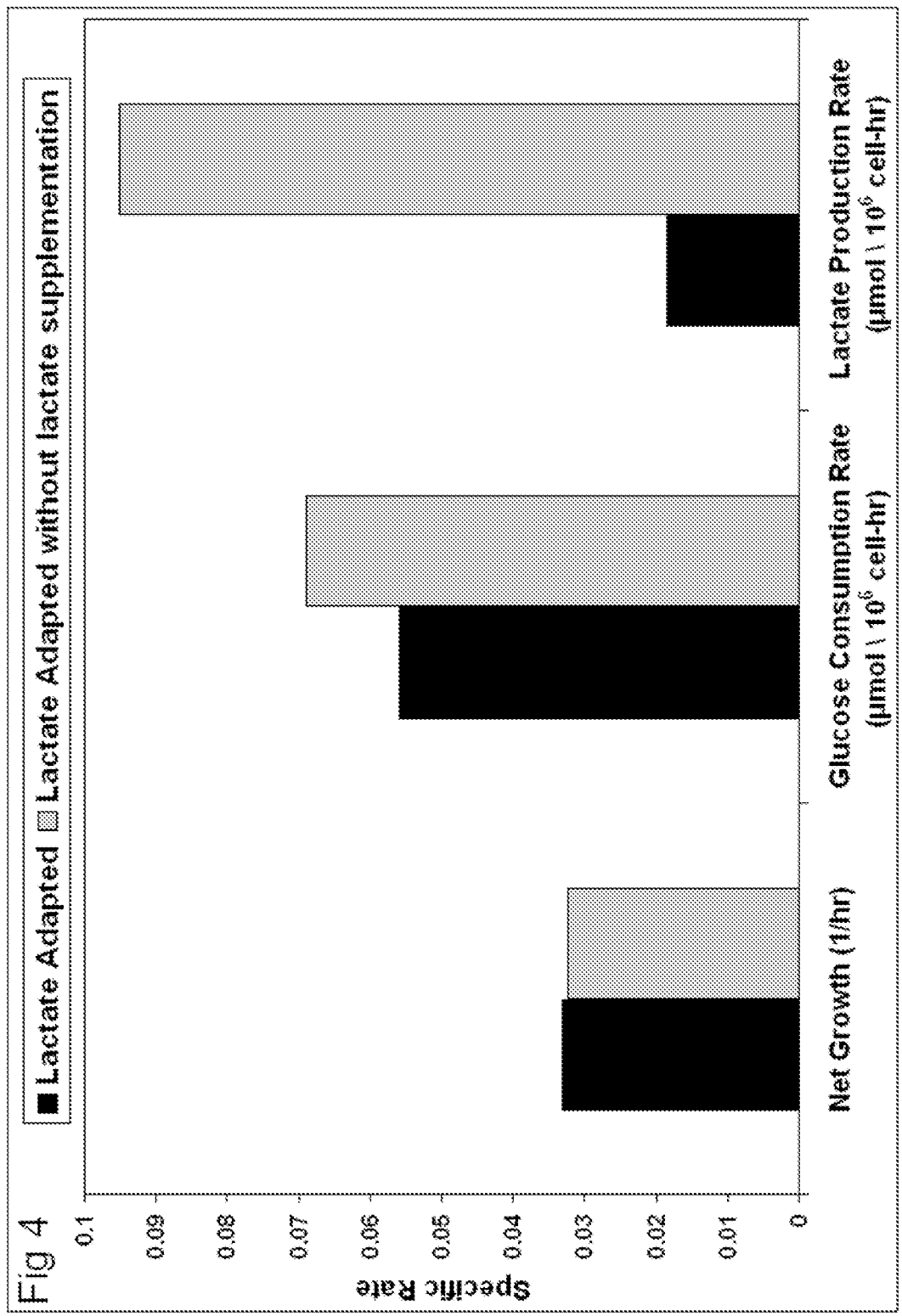

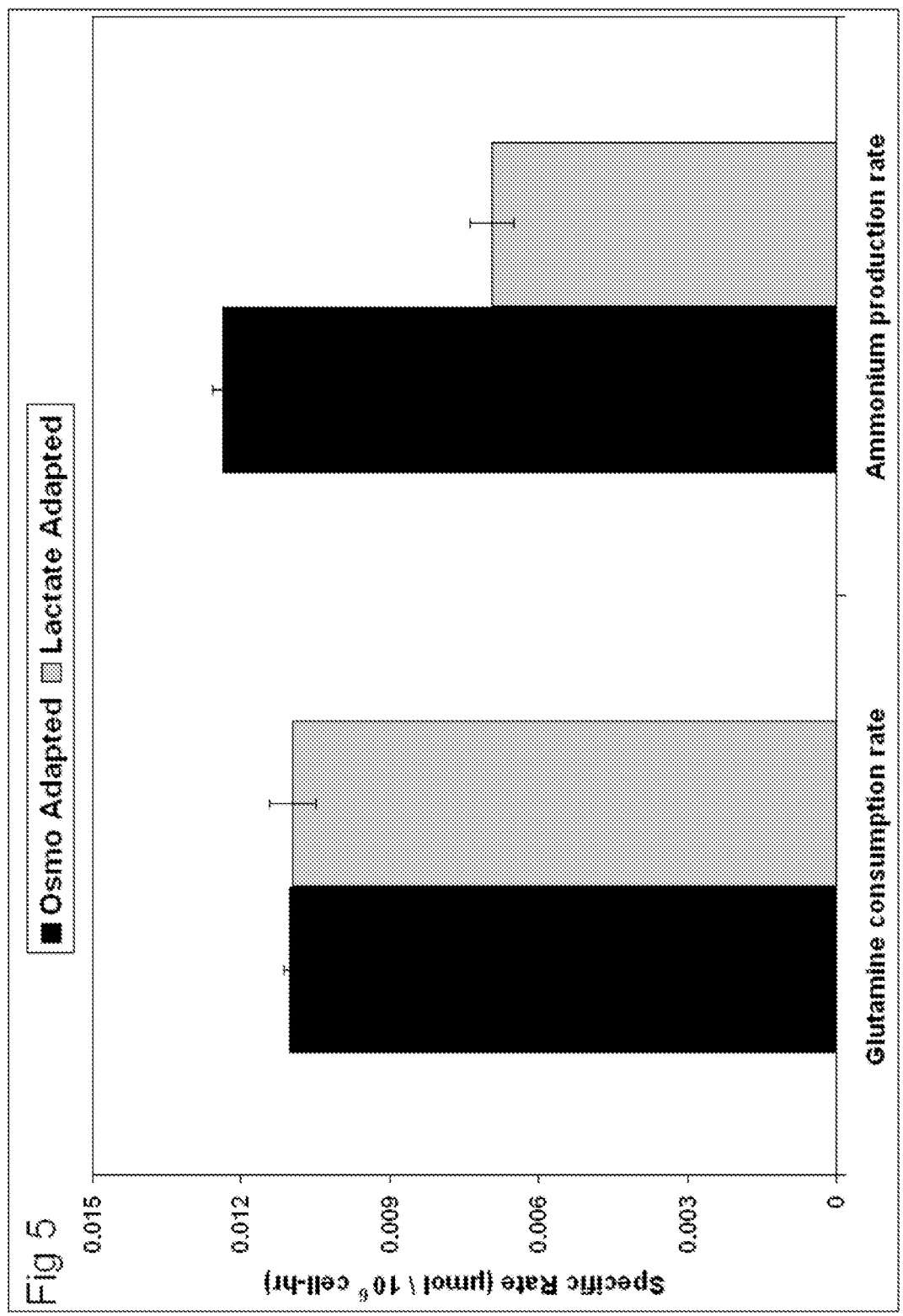

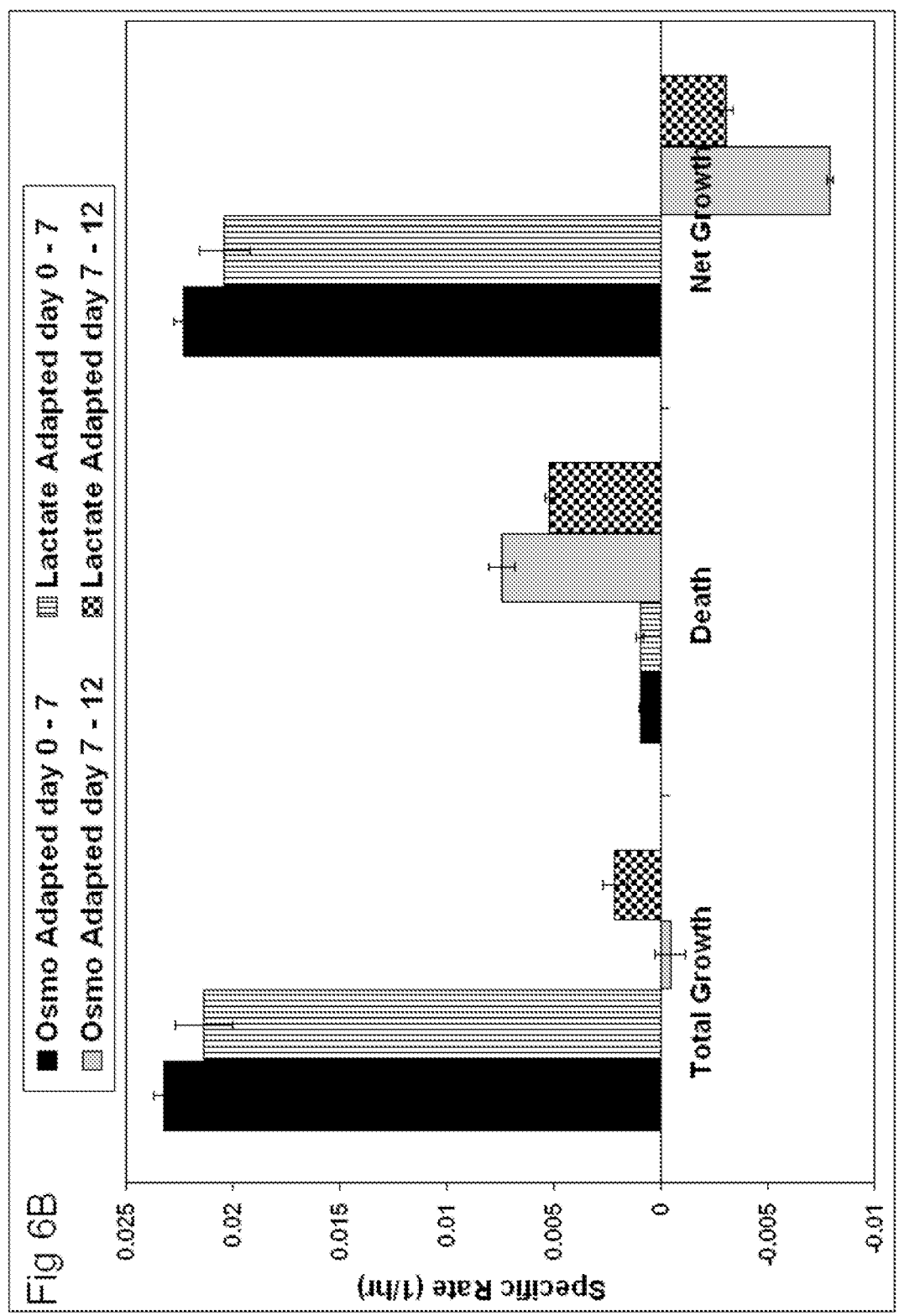

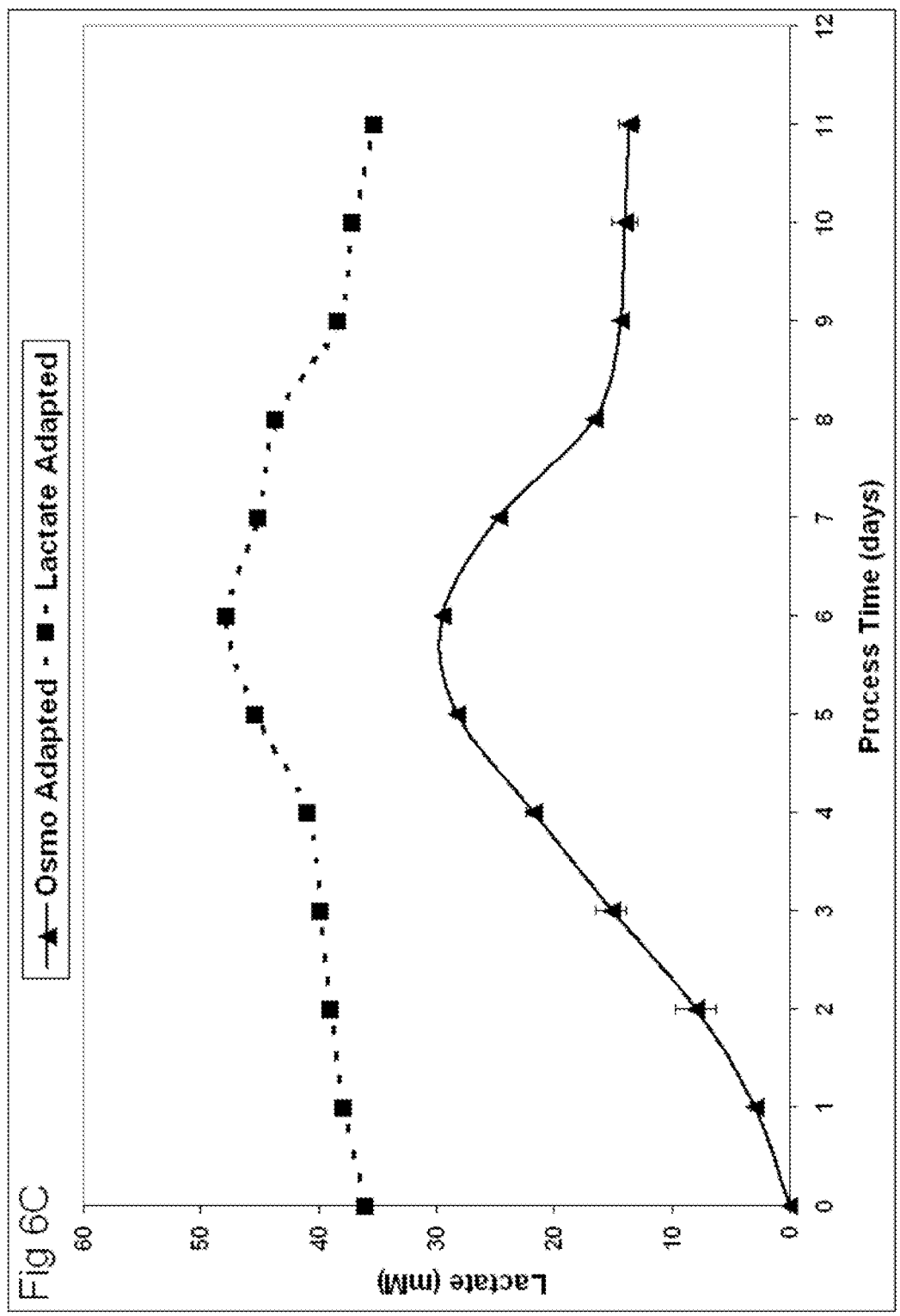

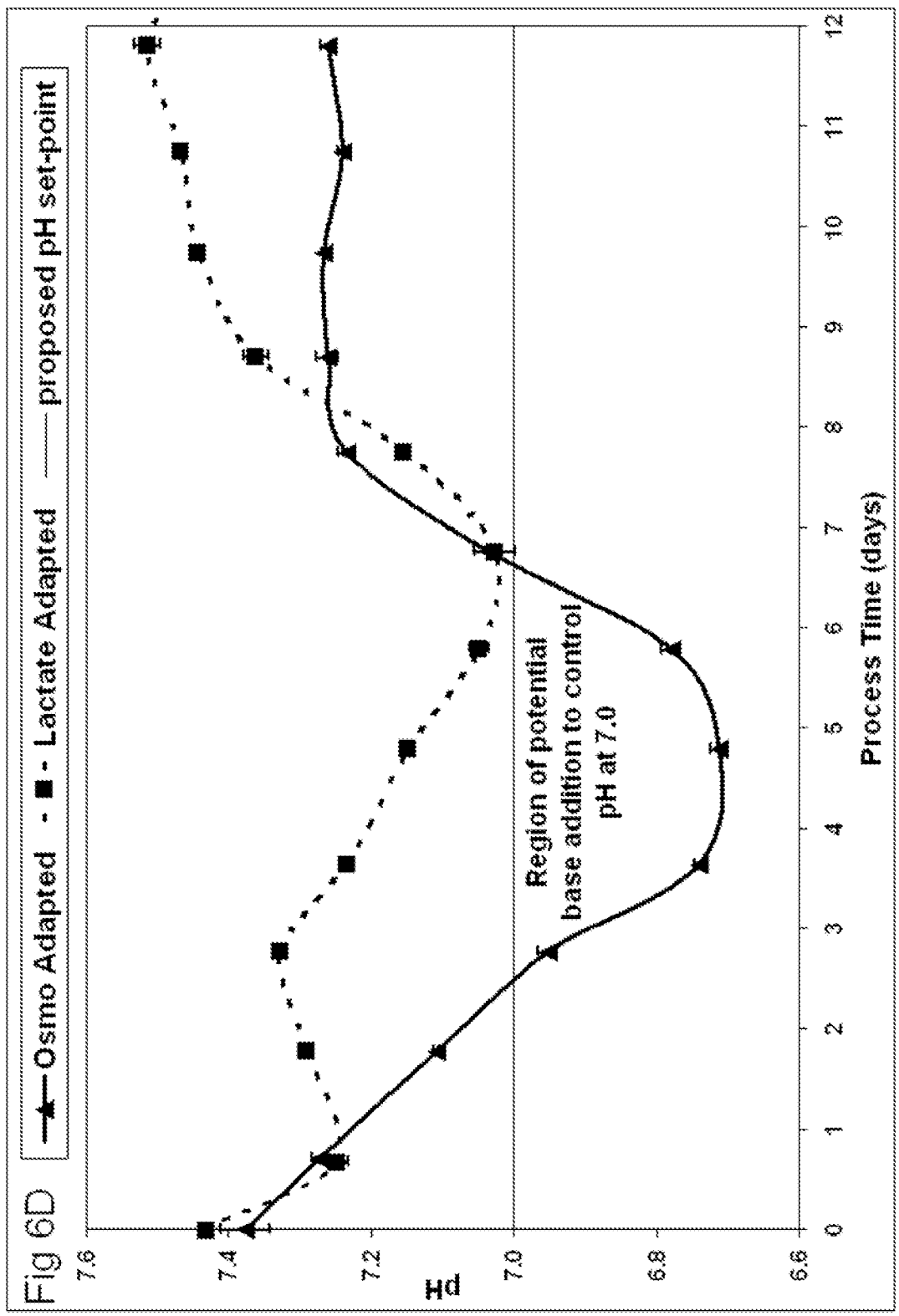

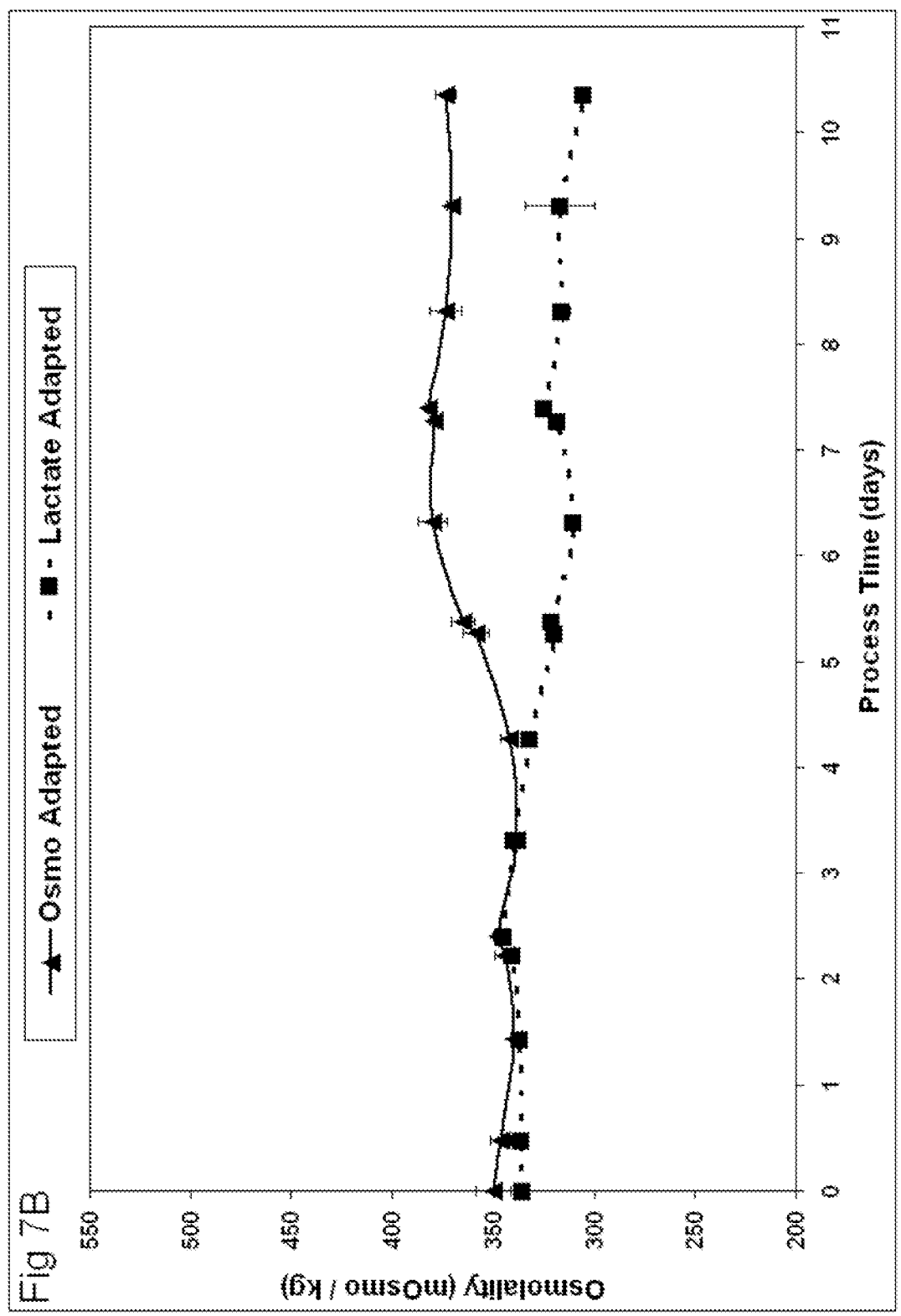

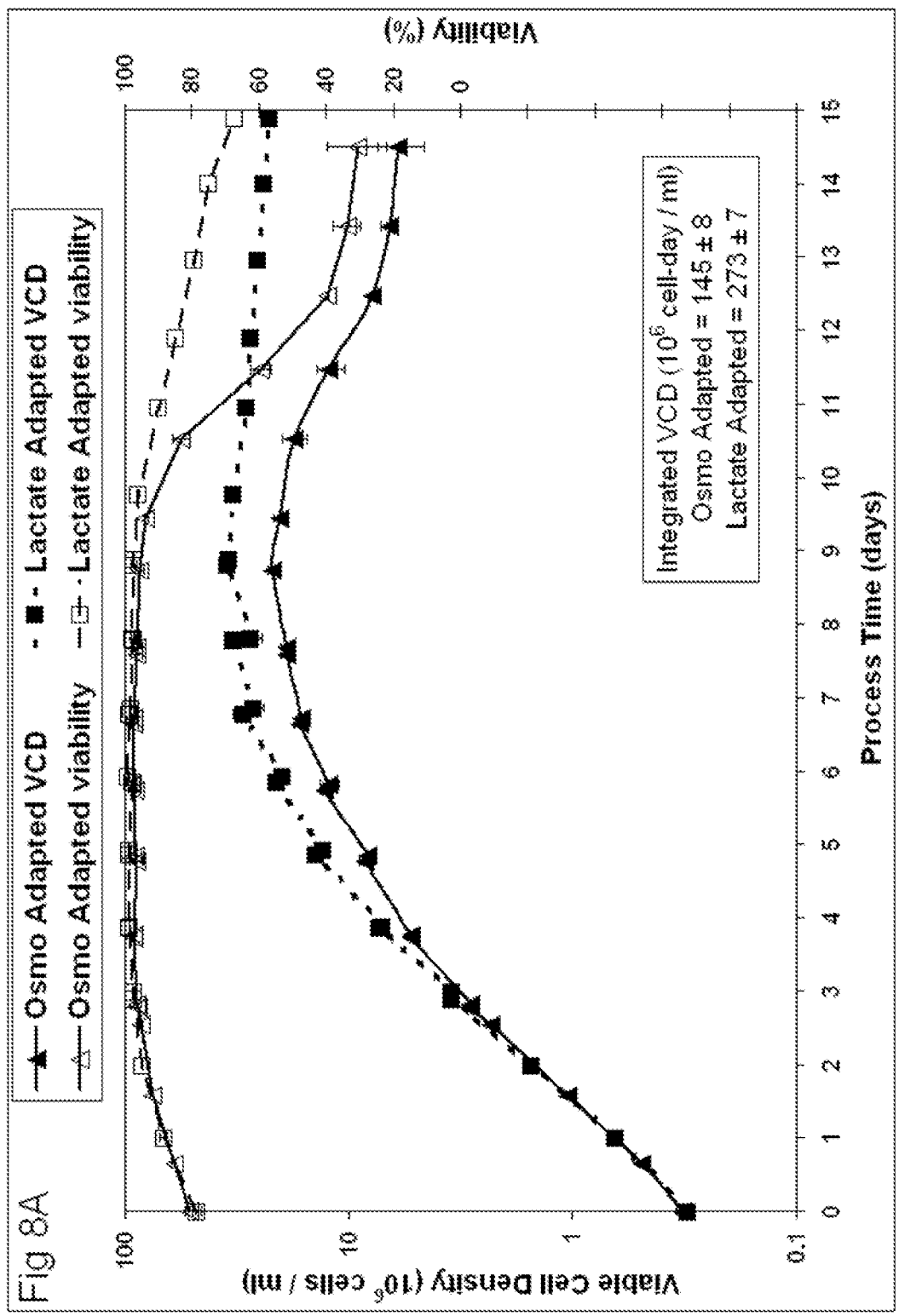

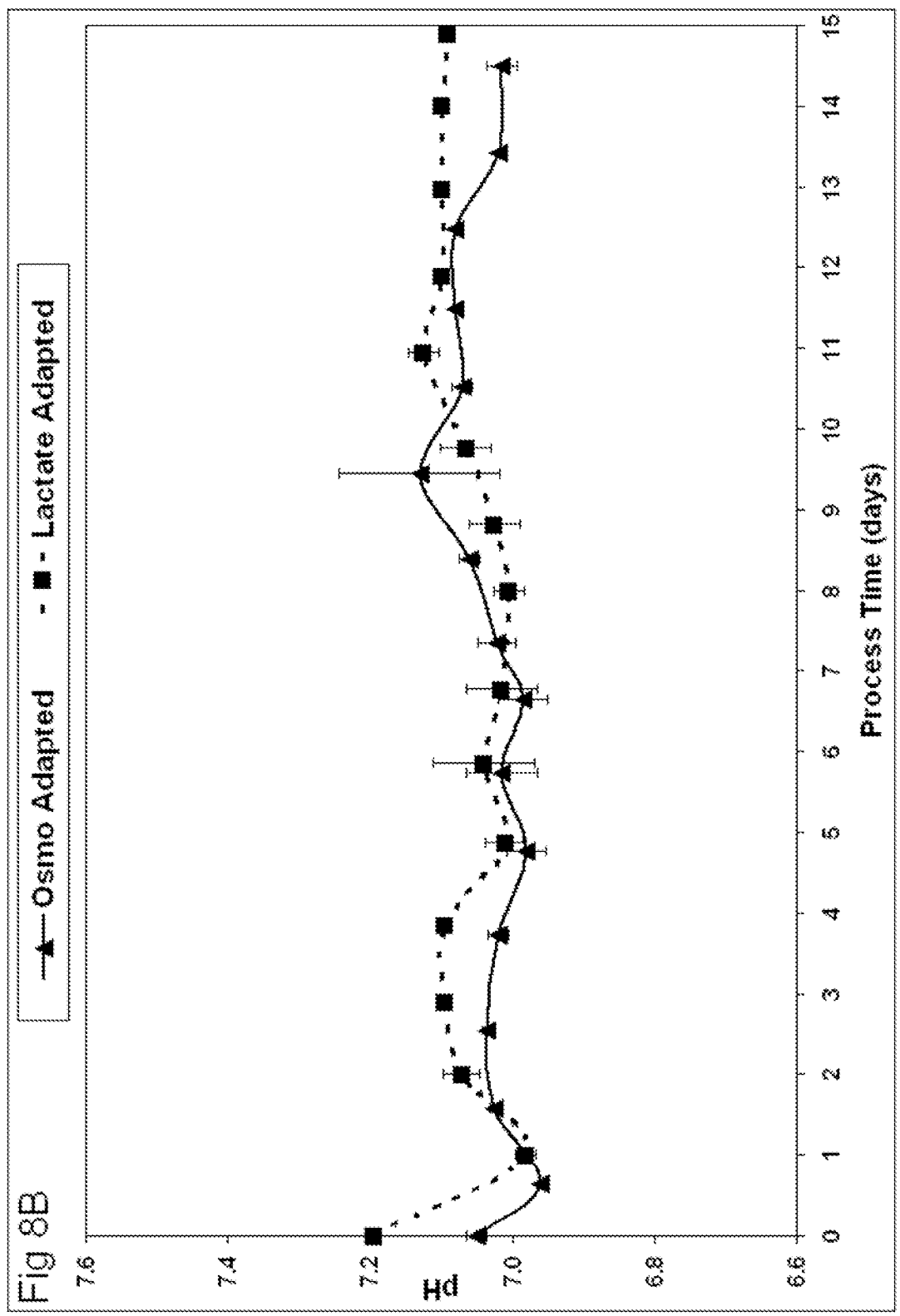

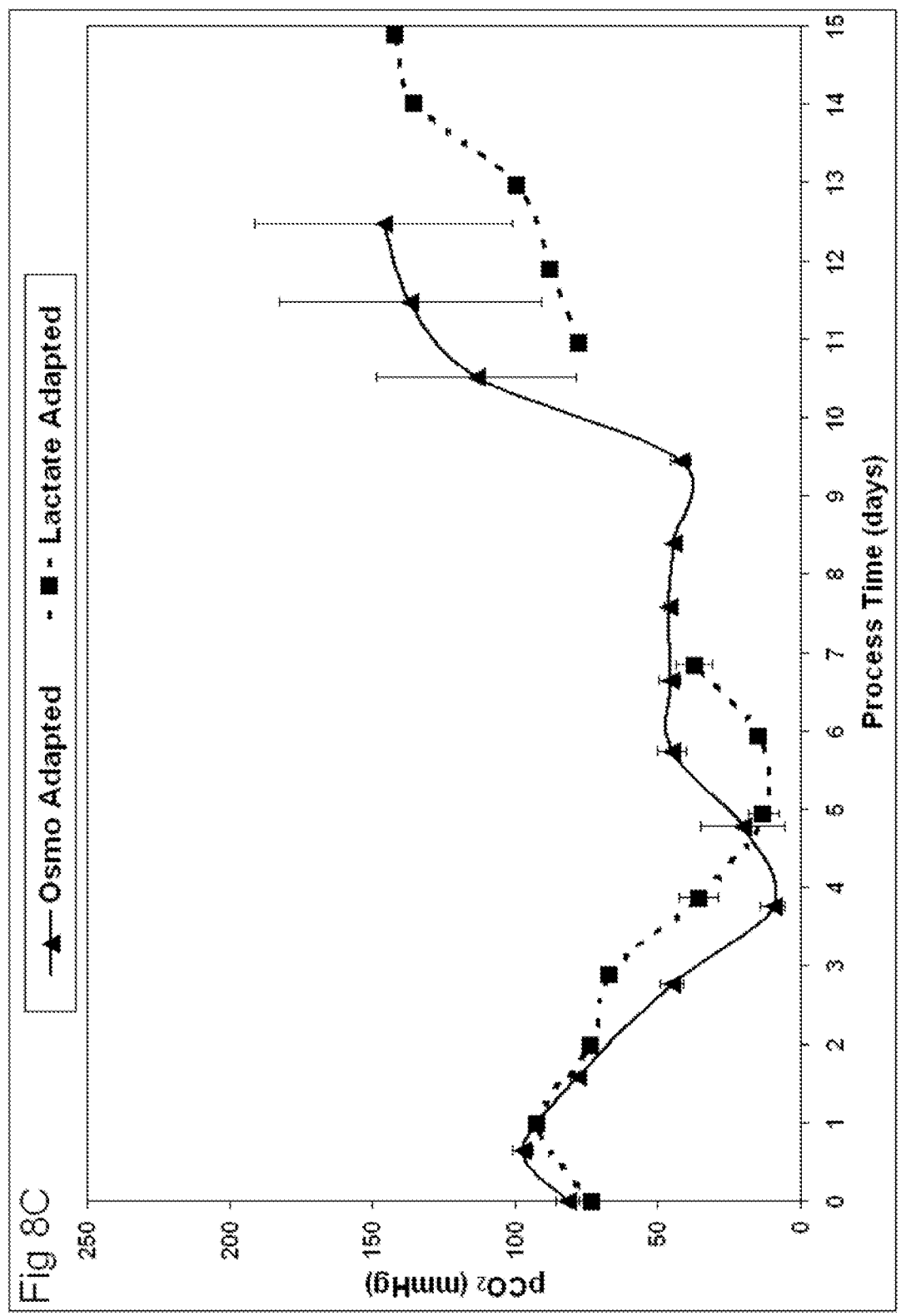

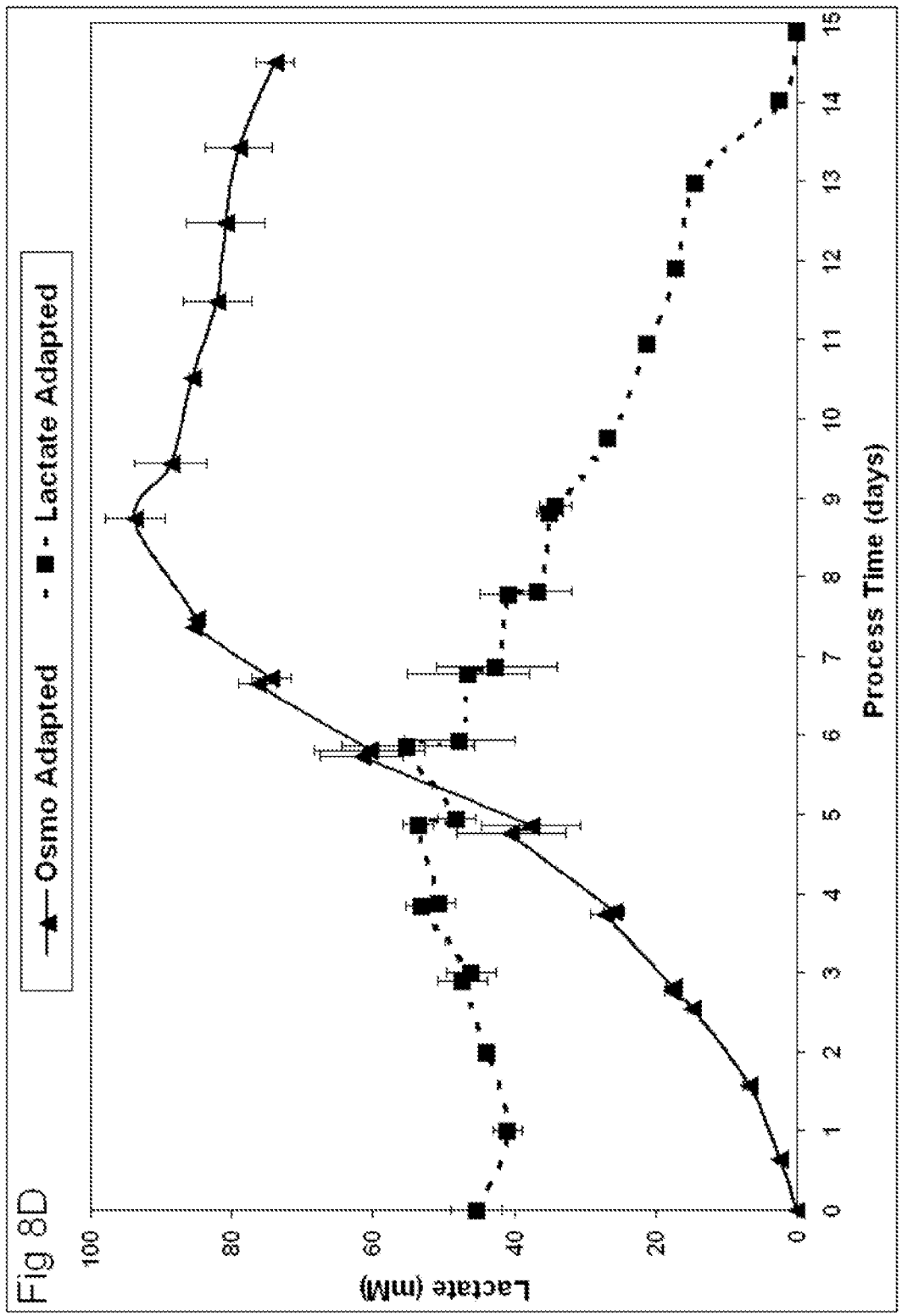

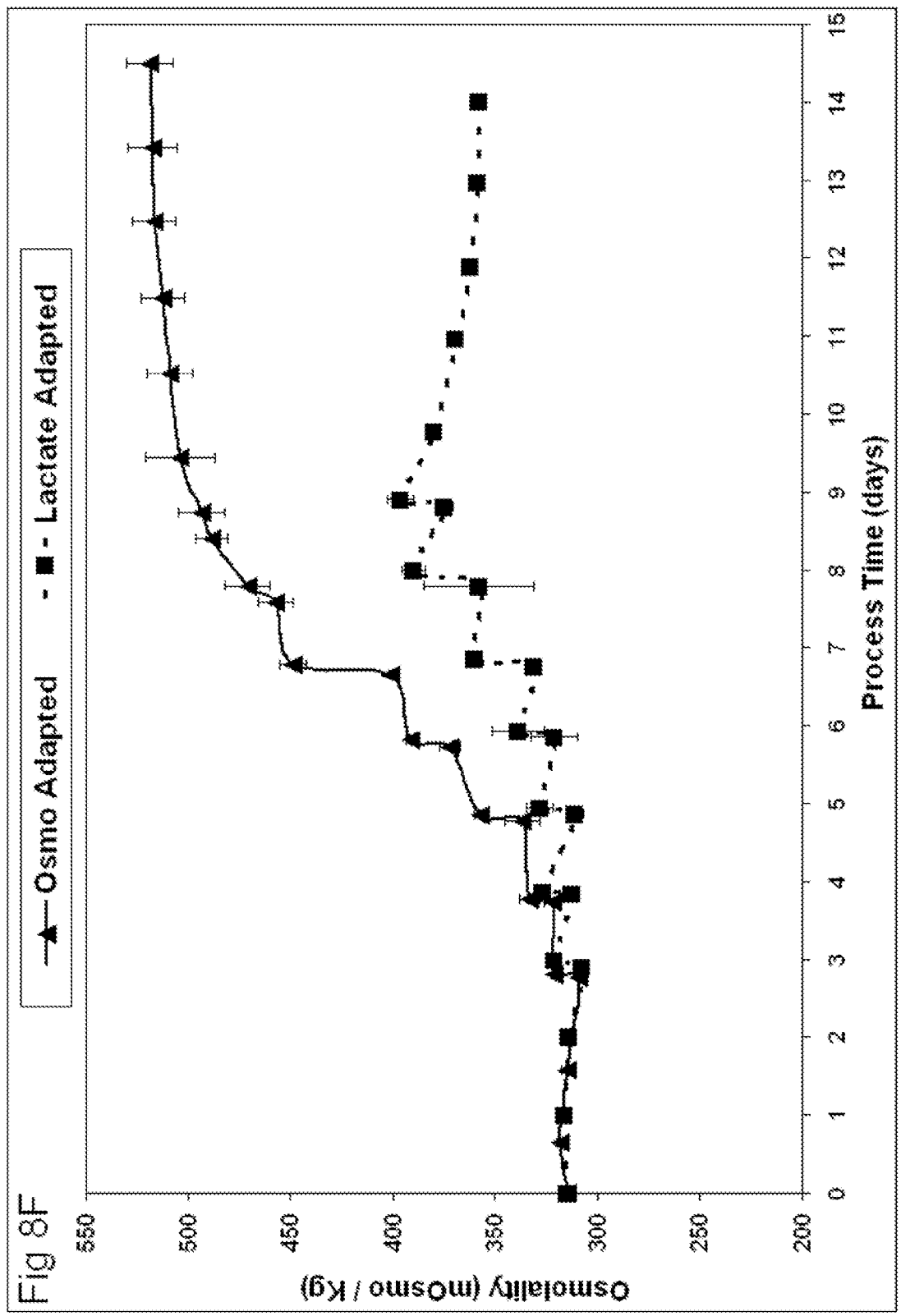

STRATEGY TO REDUCE LACTIC ACID PRODUCTION AND CONTROL PH IN ANIMAL CELL CULTURE

CROSS-REFERENCE TO RELATED APPLICATION

This application claims the benefit under 35 U.S.C. §119(e) of U.S. Provisional Patent Application No. 61/250,798 filed Oct. 12, 2009, where this provisional application is incorporated herein by reference in its entirety.

BACKGROUND

1. Technical Field

The present disclosure is related generally to methods for culturing animal cells in the presence of exogenous lactate.

2. Description of the Related Art

A number of successful methods have been developed for the commercial production of recombinant therapeutic proteins and other products using animal cell culture. The fed-batch approach is among the more popular methods, as it works well for current good manufacturing process (cGMP) operations and provides improved cell culture performance compared to the batch method. It involves minimally invasive operations and allows predictable scale-up. To sustain cell performance over time in such cultures, a strategy of providing nutrients sufficient for high cell growth, viability, and productivity becomes important. For practical reasons, and to avoid the risk of nutrient depletion, the levels of many key nutrients, such as glucose, are often above the minimum required amount. When glucose is above the minimum required amount, it is not metabolized efficiently. As a result, lactic acid is generated and can accumulate to concentrations that inhibit cell growth and recombinant protein formation (Glacken et al., *Biotechnol Bioeng.* 1988, 32:491-506; Lao and Toth, *Biotechnol Prog.* 1997, 13:688-691; Omasa et al., *Biotechnol Bioeng.* 1992, 39:556-564; Ozturk et al., *Biotechnol Bioeng.* 1992, 39:418-431). Inhibition of cell growth is often partly due to excessive increases in osmolality in pH-controlled bioreactors; this is a particular challenge for fed-batch processes where the extension of culture time can be accompanied by excessive lactic acid accumulation (Chu and Robinson, *Curr Opin Biotechnol* 12:180-1872001; Hu and Ozturk, *Cell Culture Technology for Pharmaceutical and Cell-Based Therapies.* Florida: CRC Press 2006; Meier, 2005, "Cell culture scale-up: mixing, mass transfer, and use of appropriate scale-down models", *Biochemical engineering XIV.* Harrison Hot Springs, Canada).

To meet this challenge, a number of strategies have been developed to minimize lactic acid production. Simple methods, such as control of the culture at lower pH, have been implemented in manufacturing operations, but are often insufficient. Furthermore, low pH levels may negatively impact the growth, viability, or productivity of the cells, as well as the quality of any product derived from or generated by the cells. More complicated strategies, such as feedback control of glucose at low levels (Altamirano et al., *Biotechnol Bioeng.* 2001, 76:351-360; Maranga and Goochee, *Biotechnol Bioeng.* 2006, 94:139-150; Xie and Wang, *Cytotechnology.* 1994, 15:17-29; Zhou et al., *Biotechnol Bioeng.* 1995, 46:579-587) may be considered not robust enough for implementation in actual cGMP operations. Low glucose levels may lead to glucose depletion, apoptosis, and premature cell death (Yeo et al., *Biotechnol Lett.* 2006, 28:1445-1452) or affect product quality by reducing glycosylation (Nyberg, *IBM Journal of Research and Development.* 2000, 44:770). These considerations make implementation less attractive.

Use of alternative sugars, such as fructose and galactose, and/or other glucose analogs that metabolize more slowly, produces reduced byproducts (Altamirano et al., *Biotechnol Bioeng.* 2000, 76:351-360; Duval et al., *Hybridoma.* 1992, 11:311-322) and may also lead to lower growth rates or reduced effectiveness. Metabolic engineering approaches to limiting glycolytic activity (Paredes et al. *Cytotechnology.* 1999, 30:85-93), disrupt lactate dehydrogenase (Chen et al. *Biotechnol Bioeng.* 2001, 72:55-61; Jeong et al. *Biochem Biophys Res Commun.* 2001, 289:1141-1149) or improve flux into the TCA cycle (Irani et al. *Biotechnol Bioeng.* 1999, 66:238-246) are often time consuming and have the potential for creating unstable cell lines in CHO cell cultures. These methods have improved over the years (Kim and Lee, *Appl Microbiol Biotechnol.* 2007, 74:152-159; Kim and Lee, *Appl Microbiol Biotechnol.* 2007, 76:659-665) but have not been significantly implemented in commercial processes. There still exists a need to develop a strategy that restricts lactic acid production in a simple and robust manner.

BRIEF SUMMARY

The present disclosure relates to methods for culturing cells with exogenous lactate and various uses disclosed herein. More specifically, the present disclosure relates to methods for producing a recombinant protein. In particular, the present disclosure relates to methods for controlling cell metabolism and maintaining pH stability and osmolality in animal cell cultures.

One aspect of the disclosure relates to a method for producing a recombinant protein by a cell comprising culturing the cell in a sufficient concentration of exogenous lactate to reduce lactic acid production by the cell, wherein the cell comprises a polynucleotide that encodes a recombinant protein, thereby producing the recombinant protein. In one embodiment, the sufficient concentration of lactate is about 5 to about 100 mM lactate. In a further embodiment, the sufficient concentration of lactate is about 20 to about 80 mM lactate. In another embodiment, lactate yield from glucose by the cell is less than 0.3 (mole/mole) $Y_{l/g}$. In yet another embodiment, the sufficient concentration of lactate reduces the specific lactic acid production rate of the cell by at least 50%.

In another embodiment, the exogenous lactate is one or more lactate salts or analogs selected from the group consisting of sodium lactate, potassium lactate, calcium lactate, zinc lactate, magnesium lactate, ammonium lactate, lactic acid, glycolate and 2-methyl-lactate. In a particular embodiment, the exogenous lactate is sodium lactate.

One embodiment provides that the culturing step comprises an initial cell concentration of about 0.3 to about 1.0× $10^6$ cells/ml. In another embodiment, the culturing step comprises adding exogenous lactate to the cell more than one time. In certain embodiments, the cell is cultured with glucose at a concentration of about 1 to about 12 g/L. In another embodiment, the cell produces less ammonium in the presence of the sufficient concentration of exogenous lactate than in the absence of the sufficient concentration of exogenous lactate.

In one embodiment, the cell is a Chinese hamster ovary (CHO) cell. In particular embodiments, the recombinant protein comprises an antibody, or a fragment thereof. In yet another embodiment, the step of culturing does not require an external pH control to maintain optimum cell growth and viability.

One embodiment comprises adapting the cell to the sufficient concentration of exogenous lactate prior to the culturing step, thereby producing an adapted cell capable of growing in the sufficient concentration of exogenous lactate. In a related embodiment, the adapting step comprises culturing the cell for about 4 to about 12 weeks with the sufficient concentration of exogenous lactate. In a further embodiment, the adapting step further comprises passaging said cell every 2 to 6 days. In another embodiment, the adapted cell produces less ammonium in the presence of the sufficient concentration of exogenous lactate than in the absence of the sufficient concentration of exogenous lactate.

Another aspect of the disclosure provides a method for culturing an animal cell, comprising the steps of: (a) selecting a sufficient concentration of exogenous lactate to reduce lactic acid production by the cell, wherein selecting comprises culturing the cell at various concentrations of lactate and measuring cell density; and (b) culturing the cell in the sufficient concentration of exogenous lactate. Another embodiment further comprises adapting the cell to the sufficient concentration of exogenous lactate prior to the culturing step, thereby producing an adapted cell capable of growing in the sufficient concentration of exogenous lactate.

In another embodiment, the selecting step further comprises monitoring one or more of cell growth rate, pH, and osmolality. In certain embodiments, step (a) further comprises measuring a concentration of one or more nutrients or metabolites. In particular embodiments, the one or more nutrients or metabolites are selected from the group consisting of glucose, glutamine, lactate and ammonium. In yet another embodiment, the culturing step does not require an external pH control to maintain optimum cell growth and viability. In certain embodiments, the step of culturing the cell with the sufficient concentration of exogenous lactate maintains the pH at a range from about 7.0 to about 7.5.

Yet another related embodiment further comprises infecting the cell with a viral vector in the sufficient concentration of lactate. In certain embodiments, viral vector is for a gene therapy or a vaccine.

In one embodiment, the animal cells or lactate adapted cells express a recombinant polypeptide. In a related embodiment, the recombinant polypeptide is expressed transiently. In yet another embodiment, the cell culture is a fed-batch animal cell culture. In certain embodiments, the culturing step prevents an excessive osmolality increase in the cell culture upon the addition of the concentrated nutrient feed.

BRIEF DESCRIPTION OF THE SEVERAL VIEWS OF THE DRAWINGS

FIG. 1A is a line graph that shows average viable cell density (VCD) and viability profiles for cultures grown at various initial lactate and osmolality levels.

FIG. 1B is a bar graph that shows corresponding average specific growth and death rates.

FIG. 1C is a bar graph that shows corresponding specific lactic acid production rates.

FIG. 2A is a line graph that shows specific net growth rate in Na-lactate supplemented medium as a function of adaptation time.

FIG. 2B is a line graph that shows time course profiles of initial lactate concentrations and corresponding osmolality level during adaptation.

FIG. 2C is a line graph that shows specific net growth rate after adaptation compared to Osmo Adapted cells.

FIG. 2D is a line graph that shows corresponding specific total growth and death rate profiles after adaptation compared to Osmo Adapted cells.

FIG. 3 is a dot plot that shows the effect of increasing initial lactate concentration on specific lactic acid production rate of adapted cells.

FIG. 4 is a bar graph that shows specific rates of net growth, glucose consumption, and lactic acid production in Lactate Adapted cultures when batched with or without lactate supplementation.

FIG. 5 is a bar graph that shows specific glutamine consumption rate and specific ammonium production rate of Osmo Adapted and Lactate Adapted cultures.

FIG. 6B is a bar graph that shows corresponding average specific total growth rates, death rates, and specific net growth rates of Osmo Adapted and Lactate Adapted cultures.

FIG. 6C is a line graph that shows time course profiles of residual lactate concentration in Osmo Adapted and Lactate Adapted cultures.

FIG. 6D is a line graph that shows time course profiles of pH in Osmo Adapted and Lactate Adapted cultures.

FIG. 7B is a line graph that shows corresponding time course profiles of osmolality in Osmo Adapted and Lactate Adapted cultures.

FIG. 8A is a line graph that shows the average viable cell density (VCD) and viability profiles of Osmo Adapted and Lactate Adapted cultures under pH controlled, fed-batch conditions. Cultures were fed between days 3 to 9.

FIG. 8B is a line graph that shows corresponding time course profiles of pH in Osmo Adapted and Lactate Adapted cultures.

FIG. 8C is a line graph that shows corresponding time course profiles of pCO$_2$ levels in Osmo Adapted and Lactate Adapted cultures.

FIG. 8D is a line graph that shows corresponding time course profiles of residual lactate levels in Osmo Adapted and Lactate Adapted cultures.

FIG. 8F is a line graph that shows corresponding time course profiles of osmolality in Osmo Adapted and Lactate Adapted cultures.

DETAILED DESCRIPTION

Figure 6A:
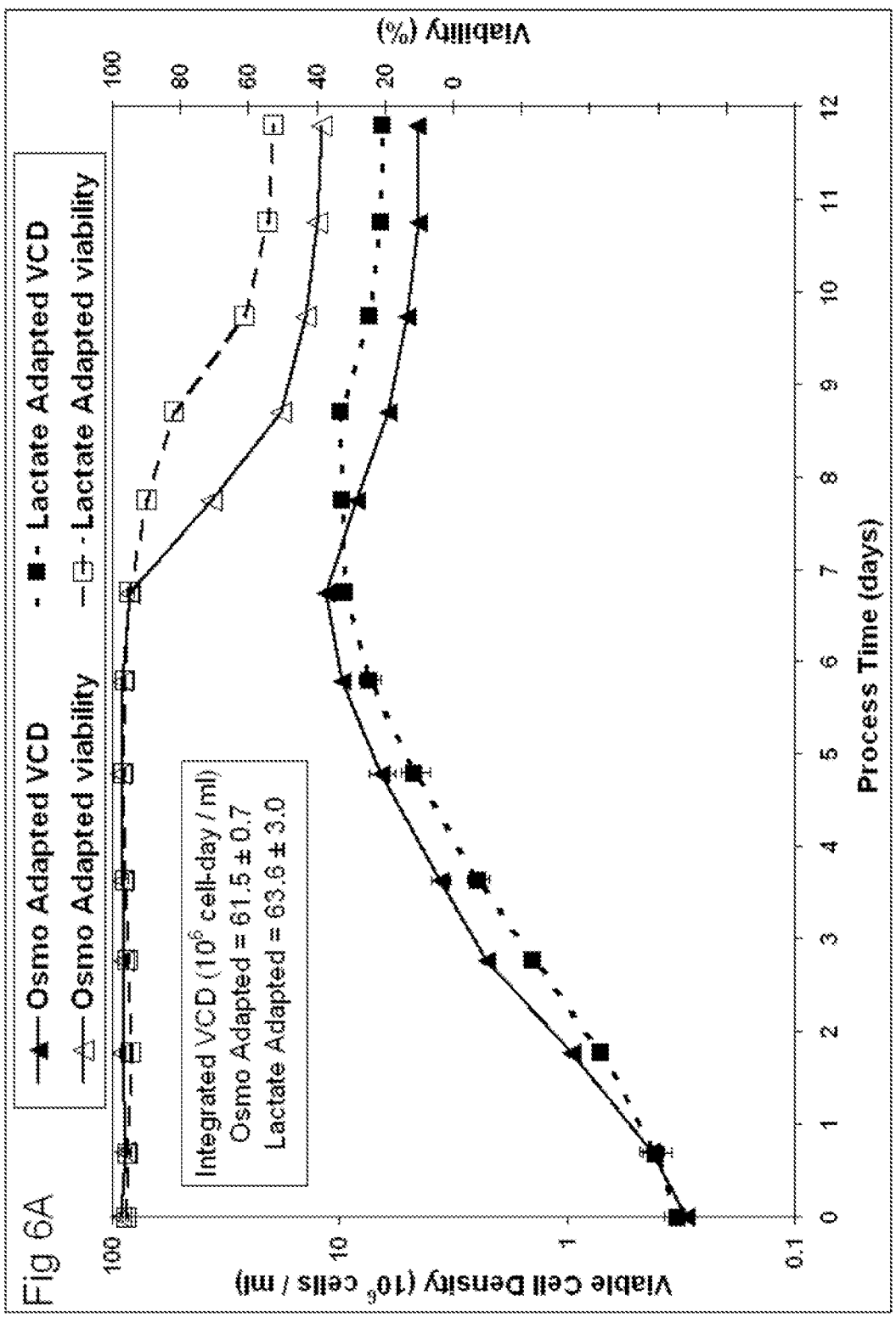
FIG. 6A is a line graph that shows the average viable cell density (VCD) and viability profiles of Osmo Adapted and Lactate Adapted cultures. The insert shows integrated viable cell density calculated by trapezoidal rule.

Through careful control of an intracellular feedback mechanism, it is demonstrated herein that inoculating cell cultures in lactate supplemented media can shift the glucose-lactate metabolic flux to zero. The quantitative impact of the lactate level on specific lactic acid production/uptake rates for a cell line was discerned. As demonstrated, this information can be used to control the metabolism of the cells, as well as pH and osmolality trajectory of the culture, by changing the lactate concentration via the addition of exogenous lactate, thereby controlling the balance of lactate consumption versus production. Although it is counter-intuitive to supplement basal culture medium with a potentially toxic metabolite, any negative effects on cell growth can be negated through adaptation as described herein.

The present disclosure provides a fast and reproducible method for culturing cells in commercially available chemically defined serum-free medium and a link to a mass action balance phenomenon to partly explain the variable nature of lactic acid metabolism in animal cell culture. The use of lactate supplemented medium formulations can be applied to practical process control challenges in high cell density fed-batch cultures, such as eliminating lactic acid production and improving pH stability to avoid hypertonic stress in pH-controlled bioreactors.

Before describing certain embodiments in detail, it is to be understood that the terms used in this specification generally have their ordinary meaning in the art. As used in the present disclosure and claims, the singular forms "a," "an," and "the" include plural forms unless the context clearly dictates otherwise. In addition, the term "about" as used herein refers to an integer and values ±15% of the integer.

Animal Cell Culture for Producing a Recombinant Product

One aspect of the disclosure relates to a method for producing a recombinant protein by a cell comprising culturing the cell in a sufficient concentration of exogenous lactate, wherein the cell comprises a polynucleotide that encodes a recombinant protein, thereby producing a recombinant protein product. A typical goal of commercial cell culture is the expression of a recombinant cell product, i.e., a peptide encoded by a recombinant DNA sequence or transgene. Prokaryotic and eukaryotic host expression systems are well known in the art. A recombinant cell product may, for example, be a therapeutic protein or a research tool. Examples of recombinant proteins include, for example, antibodies, fusion proteins, antigenic peptides, hormones, enzymes, and other known proteins and peptides that may comprise a wild type or mutant amino acid sequence.

As used herein, "exogenous lactate" refers to lactate added to the cell culture medium, i.e., exogenous lactate is not produced by the cells in culture. Exogenous lactate may be added to the culture medium in the form of a lactate salt or analog. Lactate salts include, but are not limited to, sodium lactate, potassium lactate, calcium lactate, zinc lactate, magnesium lactate, ammonium lactate, and lactic acid. Lactate analogs include, but are not limited to, glycolate and 2-methyl-lactate.

"Polynucleotide" refers to a chain of nucleic acids that are linked together by chemical bonds. Polynucleotides include, but are not limited to, DNA, cDNA, RNA, mRNA, and gene sequences and segments. Polynucleotides may be isolated from a living source such as a eukaryotic cell, prokaryotic cell or virus, or may be derived through in vitro manipulation by using standard techniques of molecular biology, or by DNA synthesis, or by a combination of a number of techniques.

Host cells transformed or transfected with a recombinant polynucleotide sequence, e.g., a transgene, are cultured under conditions suitable for the expression and recovery of the protein from cell culture. The protein produced by a recombinant cell may be secreted or contained intracellularly depending on the sequence and/or the vector used. In addition, the recombinant polypeptide may be expressed transiently. The cells may be transfected in the presence of the sufficient concentration of lactate, and/or after medium exchange or resuspension in new medium. Accordingly, cells may be transfected prior to culture in a sufficient concentration of lactate, or cells may be transfected in a sufficient concentration of lactate. If cells are to be adapted to a sufficient concentration of lactate, they can be transfected prior to, after, or during the adaptation phase.

As used herein, the term "polypeptide" is used in its conventional meaning, i.e., as a sequence of amino acids. The recombinant polypeptides produced using the method described herein are not limited to a specific length of the product; thus, peptides, oligopeptides, and proteins are included within the definition of recombinant polypeptide, and such terms may be used interchangeably herein unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof.

Within other illustrative embodiments, a recombinant polypeptide may be a fusion polypeptide that comprises multiple polypeptides. For example, fusion polypeptides may be selected so as to, e.g., increase the solubility, enable the polypeptide to be targeted to desired intracellular compartments, or facilitate purification of the polypeptide.

A polypeptide expressed as a recombinant polypeptide allows the production at increased levels in an expression system. Briefly, DNA sequences encoding the polypeptide may be assembled and ligated into an appropriate expression vector. This permits translation of the polypeptide that retains the biological activity by a host cell on a large scale.

The term "antibody" (Ab) as used herein includes monoclonal antibodies, polyclonal antibodies, multispecific antibodies (e.g., bispecific antibodies), chimeric antibodies (e.g., humanized and primatized antibodies) and antibody fragments, so long as they exhibit the desired biological activity, e.g., specifically bind antigen or bind an Fc receptor. The term "immunoglobulin" (Ig) is used interchangeably with "antibody" herein.

The basic antibody unit is a heterotetrameric glycoprotein composed of two identical light (L) chains and two identical heavy (H) chains that each contain a variable domain and a constant domain. The L chain from any vertebrate species can be assigned to one of two clearly distinct types, called kappa (κ) and lambda (λ), based on the amino acid sequences of their constant domains. Depending on the amino acid sequence of the constant domain of their heavy chains (CH), immunoglobulins can be assigned to five classes of immunoglobulins: IgA, IgD, IgE, IgG, and IgM.

An "intact" antibody is one that comprises an antigen-binding site as well as light chain and heavy chain constant domains. Preferably, the intact antibody has one or more effector functions.

An "antibody fragment" is a polypeptide comprising or consisting of a portion of an intact antibody, e.g., the antigen binding or variable region of the intact antibody. Examples of antibody fragments include Fab, Fab', F(ab')2, Fc and Fv fragments; diabodies; linear antibodies (see U.S. Pat. No. 5,641,870; Zapata et al., *Protein Eng.* 8(10): 1057-1062 [1995]); single-chain antibody molecules; and multispecific antibodies formed from antibody fragments.

Antibodies may be produced recombinantly, using vectors and methods available in the art. For example, the variable regions of a monoclonal antibody can be recovered and sequenced by standard molecular biology methods, such as RT-PCR. The polynucleotide sequences encoding the H and L chains can be cloned into a suitable expression vector known in the art and transfected into a suitable host cell (e.g., insect or mammalian cells) to secrete antibody into the culture supernatant. Antibody fragments can also be produced directly by recombinant host cells. Fab, Fv and ScFv antibody fragments can all be expressed in and secreted from a host cell, thus allowing the facile production of large amounts of these fragments.

Sufficient Concentration of Lactate

As used herein, the term "sufficient concentration of lactate" or "sufficient concentration of exogenous lactate" refers to the concentration of lactate necessary to reduce lactic acid production by a cell in culture. For example, the sufficient concentration of lactate may be about 5 to about 100 mM lactate, about 20 to about 80 mM lactate, or about 30 to about 60 mM lactate. In certain embodiments, the sufficient concentration of lactate is about 35 to 40 mM lactate. The sufficient concentration of lactate is dependent upon the cell type and specific cell line utilized. The lactate may be (D/L)-lactate, i.e., a mixture of (D)-lactate and (L)-lactate isomers, or just (L)-lactate. The relevant concentration is that of the (L)-lactate isomer. Unless otherwise indicated, the lactate concentrations described herein refer only to the (L)-lactate isomer.

In certain embodiments, the sufficient concentration of lactate reflects the maximum lactate level that can arise naturally in a normal culture system. Lactate supplementation levels may be chosen to provide certain lactic acid production and/or consumption rates. The manipulation of lactate levels as described herein can be used to control the cell metabolism, culture pH, and osmolality trajectory of the cell culture.

Various animal cell lines that may be used to generate a recombinant cell product are known in the art and include, but are not limited to, Chinese hamster ovary (CHO) cells, myeloma cells (e.g., the mouse myeloma cell line NS0), baby hamster kidney (BHK) cells, and hybridomas. As used herein, "cell line" is used in its conventional meaning, i.e., an immortalized cell line.

Lactate yield from glucose ($Y_{l/g}$) is one measurement that can be utilized to determine the sufficient concentration of lactate for the cell type to be used. $Y_{l/g}$ is a quotient describing metabolic efficiency measured as moles lactate produced per mole glucose consumed. The theoretical maximum lactate yield from glucose is 2.0, and a lower $Y_{l/g}$ indicates that more glucose is oxidized, thereby indicating if the mass action balance is skewed toward little or no lactic acid production by the cells. For example, lactate yield from glucose by the cell with a sufficient concentration of lactate is less than about 0.5, 0.4, or 0.3 $Y_{l/g}$.

Furthermore, the specific lactic acid production rate of the cells may also be calculated to determine a sufficient concentration of lactate for the cell line to be utilized. For example, the sufficient concentration of lactate reduces the specific lactic acid production rate of the cell by at least 20%, 30%, 40%, 50%, 60%, 70%, 80%, 90% or more. In certain preferred embodiments, the sufficient concentration of lactate reduces the specific lactic acid production rate by at least 50%.

The exogenous lactate added to the cell culture medium may be one or more lactate salts or analogs. For example, lactate salts include, but are not limited to, sodium lactate, potassium lactate, calcium lactate, zinc lactate, magnesium lactate, ammonium lactate, and lactic acid. Lactate analogs include, but are not limited to, glycolate and 2-methyl-lactate. In certain preferred embodiments, the exogenous lactate is sodium lactate.

The initial cell concentration inoculated with the sufficient concentration of lactate is about 0.3 to about $1.0 \times 10^7$ cells/ml, or more preferably about 0.3 to about $1.0 \times 10^6$ cells/ml. The exogenous lactate can be added to the cell culture at one time, or the exogenous lactate can be added to the cell culture at more than one time.

According to the present disclosure, the cells do not need to be cultured in media that contains a limited concentration of glucose in order to prevent lactic acid production. For example, the culture medium contains glucose at a concentration of about 1 to about 12 g/L, about 2 to about 10 g/L, about 4 to about 8 g/L, or about 4 to about 6 g/L glucose.

Another benefit that arises from taking advantage of the mass action balance is that the cells produce less ammonium ($NH_4^+$) in the presence of the sufficient concentration of exogenous lactate than in the absence of the sufficient concentration of exogenous lactate. Ammonium can negatively impact cell growth, as well the culture productivity and/or product quality (McQueen and Bailey, *Biotechnol Bioeng.*, 1990, 35:1067-1077; Ozturk et al, *Biotechnol Bioeng.*, 1992, 39:418-431; Yang and Butler, *Biotechnol Bioeng.*, 2000, 68:370-380). Therefore, culturing cells in a sufficient concentration of lactate can reduce the negative impacts of ammonium.

The sufficient concentration of lactate can reduce the amount of ammonium produced by the cells by at least 20%, 30%, 40%, 50%, 60%, 70%, 80%, 90% or more. In certain preferred embodiments, the sufficient concentration of lactate reduces the amount of ammonium produced by at least 40%.

Furthermore, the cell culture environment having a sufficient concentration of lactate is more stable with regard to osmolality, which is a problem that is faced when introducing media with a high nutrient concentration in traditional cell culture practices.

Adapting Cells to a Sufficient Concentration of Lactate

Lactic acid (2-hydroxypropanoic acid), also known as milk acid, is a carboxylic acid with the chemical formula $C_3H_6O_3$. In solution at physiological pH, it loses a proton to produce the lactate ion $CH_3CH(OH)COO^-$. Lactic acid is produced through glycolysis of glucose, under aerobic and/or anaerobic conditions, and it is a potentially toxic metabolic product. Some cell lines may need to be adapted to a high, i.e., sufficient, concentration of lactate in order to grow at a similar rate to cells grown without exogenous lactate.

Therefore, the methods of the disclosure may further comprise adapting the cell to the sufficient concentration of exogenous lactate prior to culturing the cell, thereby producing an adapted cell capable of growing in the sufficient concentration of exogenous lactate. The cells can be adapted to the high lactate concentration and overcome any negative effects via sequential passages at the sufficient concentration of lactate. For example, adapting the cells may comprise culturing the cells for about 2 to about 20 weeks, about 4 to about 16 weeks, about 4 to about 12 weeks, or about 6 to about 8 weeks with the sufficient concentration of exogenous lactate. During the adaptation phase, cells can be passaged, for example, every 1 to 7 days, every 2 to 6 days, or about every 3 to 5 days.

The specific net growth rate of cells that require adaptation to the sufficient concentration of lactate will be significantly decreased in comparison to that of cells grown without the sufficient concentration of lactate. Once the specific net growth rate of the cells being sequentially passaged in the sufficient concentration of lactate approaches or surpasses the average specific net growth rate of cells grown without exogenous lactate, the cells are considered to be fully adapted cells and may be selected for further culturing in the sufficient concentration of lactate as described herein. The adapted cells produce less lactic acid and ammonium in the presence of the sufficient concentration of exogenous lactate than in the absence of the sufficient concentration of exogenous lactate.

In certain aspects, the steps of selecting the sufficient concentration of exogenous lactate and adapting the cells to the sufficient concentration of lactate occur simultaneously. For example, groups of cells can be cultured with various concentrations of lactate to determine which concentration of lactate is the sufficient concentration necessary to reduce lactic acid production by the cell, and while monitoring the cells (e.g., monitoring one or more of the following: growth rate, viable cell density, metabolites, nutrients, pH, and osmolality), the cells are sequentially passaged for a period of time that allows the cells to adapt to the concentration of exogenous lactate present in the cell culture medium.

Adapted cells may be used immediately for cell culture as described herein, or they adapted cells may be frozen and stored for culturing at a later time.

Controlling Lactic Acid Production

As described above, lactic acid is a potentially toxic metabolic product when it accumulates in conventional cell culture conditions. Another aspect of the disclosure provides a method for culturing an animal cell by culturing the cell in the sufficient concentration of exogenous lactate, thereby controlling lactic acid production by the cell. The sufficient lactic acid concentration that reduces the lactic acid production by the cell can be selected as described above. In some instances it may be necessary to adapt the cells to the sufficient concentration of exogenous lactate prior to culturing the cells in order overcome any negative effects of the high concentration of lactic acid.

The present disclosure further contemplates a method for culturing an animal cell in culture, wherein the animal cell is infected with a viral vector. Upon infection with a viral vector, cells in culture frequently produce an increased amount of lactic acid. Therefore, culturing the cells in the sufficient concentration of lactate provides a mechanism for controlling the amount of lactic acid produced by cells infected with a viral vector.

The cells may be used to amplify the viral vector for use in a gene therapy or a vaccine. In other embodiments, the cell may be infected with the viral vector in a cell culture setting for gene therapy or a vaccine. "Gene therapy" refers to the use of an attenuated virus as a vector to introduce a particular polynucleotide sequence into a cell. As used herein, the terms "viral vector vaccine" and "viral vaccine" refer to the use of an attenuated virus encoding a peptide from a pathogen to introduce the pathogenic peptide to the immune system of the subject to be immunized. As used herein, an "infected cell" refers to a cell that has been contacted with the viral vector, and "infecting" refers to introducing the viral vector to the cell in culture.

Both cell lines (e.g., diploid and aneuploid cells) and primary cells (e.g., germ cells and somatic cells) may be infected with the viral vector. As used herein, "primary cell" is used in its conventional meaning, i.e., a cell derived from a biological sample. Various animal cell lines that may be used to amplify a viral vector are known in the art and include, but are not limited to, Vero cells, WI-38 cells, Per.C6 cells, and chicken embryo fibroblasts. Viral vectors include, but are not limited to, retroviruses, lentiviruses, adenoviruses, and adeno-associated viruses.

Improving pH Stability

Generally, an increased production of lactic acid by cells in culture results in a drop in pH, the measure of the acidity or alkalinity of a solution defined as the cologarithm of the activity of dissolved hydrogen ions ($H^+$), unless base is added to the culture and/or, in some limited circumstances, more carbon dioxide is removed through increased gas exchange. Culturing cells with the sufficient concentration of lactate provides a further benefit of improving the pH stability of the cell culture environment. Generally, commercial cell culture requires an external pH control system to maintain the pH of the culture. A pH control system may continuously or periodically monitor the pH of the culture and, for example, add base to the culture if the pH falls below a predetermined set point. However, when culturing cells in the sufficient concentration of exogenous lactate, an external pH control system, such as a system comprising an on-line probe and feedback control unit, may not be necessary to maintain optimum cell growth and viability. For example, culturing the cells with the sufficient concentration of exogenous lactate maintains the pH at a range from about 6.8 to about 7.7, about 6.9 to about 7.6, or most preferably, about 7.0 to about 7.5.

When external pH control systems are used, the pH of the culture is measured, compared to a target set point, and liquid bases and/or increased carbon dioxide removal is used to bring the pH up to the set point, or liquid acids and/or reduced carbon dioxide removal and/or carbon dioxide addition is used to bring the pH down to set point. These control systems add a substantial level of complexity and expense, particularly when smaller-scale and/or disposable (single use) bioreactors are used. They also occasionally fail and result in the loss of a production batch. The systems are most commonly used to keep the pH from going too low. The most common liquid bases used are about 1 M sodium carbonate and about 1 N sodium hydroxide. As these base solutions have much higher osmolalities than the typical range of 270-400 mOsmol/kg used for cell culture medium, addition of these bases increases the osmolality of the culture. This may reduce the amount of nutrients that can be added without an excessive osmolality increase. Furthermore, high amounts of base addition can also directly lead to excessive osmolality increases and reduced cell growth and productivity, or even cell death.

Preventing Excessive Osmolality Increase

Osmolality is a measure of the osmoles of solute per kilogram of solvent (osmol/kg). Typically, when nutrient rich culture medium, i.e., a concentrated nutrient feed, is introduced to a cell culture, it may raise the osmolality to a level that adversely affects cell growth and viability. As such, the amount of nutrients that can be added is limited. This, in turn, limits the total cell growth and productivity. These limitations can be partly overcome, and thus more nutrients added, by growing cells in a concentration of lactate that is sufficient to cause or increase lactic acid uptake by the cells, i.e., shift the mass action balance toward the consumption of lactic acid. Every mole of lactate consumed contributes to an osmolality decrease.

For example, preventing an excessive osmolality increase in a fed batch animal cell culture upon the addition of a concentrated nutrient feed may be accomplished by selecting a sufficient concentration of exogenous lactate to cause lactic acid uptake by a cell and culturing the cell with the sufficient concentration of exogenous lactate. In certain embodiments, culturing the cells does not further require an external pH control, such as a liquid base, to maintain optimum cell growth and viability.

EXAMPLES

Unless otherwise noted, the experiments described herein were conducted with a dihydrofolate reductase deficient ($DHFR^-$) Chinese Hamster Ovary cell line, DG44 CHO (Invitrogen, Carlsbad, Calif.). Prior to experimentation, the cells were transfected with a pOPTI-Vec TOPO plasmid vector containing the gene for a recombinant monoclonal ScFv-Fc1 protein fragment. Transfected cells were grown in selective OptiCHO medium (Invitrogen, Carlsbad, Calif.) and the recombinant gene copy number was further amplified by supplementing the medium with 250 nM methotrexate. The amount of recombinant antibody fragment expressed was less than 10 mg/L and not subsequently measured. This cell line was used to test the feasibility of the novel approach in terms of cell growth, death, and metabolism. Cells were frozen down and hereafter referred to as "Native Control" cells. All subsequent experiments were performed without methotrexate.

Cell concentration and viability was measured by the trypan blue exclusion method using a ViCell analyzer (Beckman Coulter, Fullerton, Calif.). Off-line measurements were taken with a Bioprofile 400 (Nova Biomedical, Waltham, Mass.) for glucose, glutamine, lactate, carbon dioxide, oxygen, ammonium concentration and pH levels. Osmolality was measured by freezing point depression on a Model 3250 Osmometer (Advanced Instruments, Norwood, Mass.)

In the first set of experiments, illustrated in FIGS. 1-6, cultures were grown at 30 ml working volume in 125 ml shaker flasks (Corning, Lowell, Mass.) placed in an incubator at 37° C., 135 rpm, and 8% $CO_2$. Continuous passages were performed every 3 to 4 days in duplicate shaker flasks inoculated at a seeding density of $1.0 \times 10^6$ cell/ml. After the cells were adapted to the high lactate concentration, longer-duration batch cultures were performed in triplicate shaker flasks for 12 days starting at a seeding density of $0.3 \times 10^6$ cells/ml. A sodium (D/L)-lactate stock solution (Sigma, Lowell, Mass.) was used for lactate supplementation. All reported lactate values are for the physiologically relevant L-Lactate isomer.

In the second set of experiments, illustrated in FIGS. 7 and 8, cultures were grown in identically configured 3 L Applikon bioreactors in duplicate with an initial working volume of 1.6 L. The bioreactors consisted of a rounded bottom glass vessel and stainless steel head plate with gas ports for sparging, overlay, and exhaust, five medium addition ports, sampling port, base and antifoam inlet, pH, dissolved oxygen (DO), and temperature probe. Temperature was controlled at 37° C., pH was controlled at 7.05 with a dead band of 0.03 using $CO_2$ gas sparging or 1.0 M sodium carbonate solution (Ricca Chemical Company.) DO was controlled at 50% air saturation. A 3-bladed marine impeller was set at 250 rpm between days 0 and 3. Agitation was increased to 300 rpm on day 4. Oxygen tension was maintained through the use of a drilled tube sparger. Air sparging was used between days 0 and 4 then switched to oxygen sparging on day 5. Flow rate was controlled with rotameters and maintained to provide adequate oxygen tension and carbon dioxide stripping.

Furthermore, in the second set of experiments, cultures were grown in a custom-ordered version of the commercially-available, serum-free, chemically-defined OptiCHO basal medium (Invitrogen, Carlsbad, Calif.) This basal medium was custom ordered free of glucose and NaCl. This basal medium was then supplemented with 8 mM glutamine (Invitrogen, Carlsbad, Calif.), 5.8 g/L glucose (Invitrogen, Carlsbad, Calif.), antifoam (Sigma, Lowell, Mass.), and 40 mM Na-lactate (Sigma, Lowell, Mass.) for the Lactate Adapted cell line or 40 mM NaCl (Sigma, Lowell, Mass.) for the Osmo Adapted cell line. A sodium (L)-lactate stock solution (Sigma, Lowell, Mass.) was used for this set of experiments. All reported lactate values are the physiologically relevant L-lactate isomer.

Bioreactors were batched with basal medium, allowed to reach temperature, pH, and DO set point, then inoculated at a seeding density of $0.3 \times 10^6$ cells/ml. Feed solutions included a combination of glucose, glutamine, amino acids, growth factors, nucleosides, vitamins, trace elements, and salts. Feed solutions were not supplemented with Na-Lactate or NaCl. All off-line sample analysis was performed as previously described.

Specific rates were determined on a time interval bases by measuring daily viable and total cell density (VCD or TCD) and metabolite concentrations. Specific net growth rate ($\mu_N$), was calculated as change in VCD over a time interval $t_1$ to $t_2$ using Equation 1:

$$\mu_N = \frac{\ln[VCD_2/VCD_1]}{t_2 - t_1} \quad (1)$$

Specific total growth rate ($\mu_T$) and death rate (Kd) were determined in the same time interval using Equations 2 to 4:

$$\mu_T = \mu_N \left( \frac{TCD_2 - TCD_1}{VCD_2 - VCD_1} \right) \text{ for } VCD_1 \neq VCD_2 \quad (2)$$

$$\mu_T = \left( \frac{\frac{TCD_2 - TCD_1}{VCD_1}}{t_2 - t_1} \right) \text{ for } VCD_1 = VCD_2 \quad (3)$$

$$Kd = \mu_T - \mu_N \quad (4)$$

Metabolic flux was calculated as specific nutrient consumption rate or specific metabolite production rate ($q_p$) using Equations 5 and 6, where P is nutrient such as glucose or glutamine or metabolite such as lactic acid or ammonium) concentration:

$$q_P = \mu_N \left( \frac{P_2 - P_1}{VCD_2 - VCD_1} \right) \text{ for } VCD_1 \neq VCD_2 \quad (5)$$

$$q_P = \left( \frac{\frac{P_2 - P_1}{VCD_1}}{t_2 - t_1} \right) \text{ for } VCD_1 = VCD_2 \quad (6)$$

Error bars indicate one standard deviation. JMP® software was used for statistical analysis.

Example 1

Selecting a Sufficient Concentration of Lactate

In order to test a novel strategy of minimizing lactic acid production by viewing lactic acid metabolism as a mass action balance between pyruvate and lactate levels, cells were cultured in the presence of exogenous lactate. Although the equilibrium balance highly favors lactic acid production ($\Delta G° = -25.1$ kJ/mol) this flux can hypothetically be reversed by high levels of lactate as explained by the following reaction (Lehninger, 2000, *Principles of Biochemistry*. New York: Worth Publishers):

Pyruvate to lactate interconversion     Reaction 1
and its standard free energy change.

Pyruvate + $NADH + H^+$ 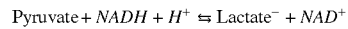 Lactate$^-$ + $NAD^+$ $$\Delta G = RT\ln K_{eq} + RT\ln\left(\frac{[LAC^-] \cdot [NAD^+]}{[PYR] \cdot [NADH]}\right)$$

Where $RT\ln K_{eq} = \Delta G° = -25.1$ kJ/mol

Lactate concentrations that increase the stoichiometric ratio above the equilibrium constant, $K_{eq}$, should generate a positive ΔG and change the actual free energy to favor pyruvate production. This phenomenon follows the laws of mass action, and thus dictates that the balance of lactate consumption versus production can be controlled by simply changing lactate levels.

Native control cells were grown in various levels of Na-lactate and NaCl to evaluate the impact each component had on growth and viability. Media compositions are discussed in Table 1. In these non-adapted cells, a clear reduction in viable cell density (VCD) was observed with increasing lactate levels (FIG. 1A). As shown in FIG. 1B, Na-lactate impacted specific total growth and death rate the most, leading to a significant drop in specific net growth. These results indicate that there is a clear inhibitory effect of lactate beyond hyperosmotic stress.

TABLE 1

Measured sodium, (L)-lactate, and osmolality levels on day 0

| Condition | Starting Level in Culture | | Starting Osmolality |
|---|---|---|---|
| | $Na^+$ (mM) | (L)-lactate (mM) | (mOsmo/kg) |
| Native control | 160 | 0 | 270 |
| Osmo ctrl | 223 | 0 | 350 |
| 27 mM Lac | 227 | 27 | 356 |
| 40 mM Lac | 238 | 40 | 372 |

The impact lactate supplementation had on lactic acid metabolism is shown in FIG. 1C. There was a dramatic drop in specific lactic acid production at 27 mM lactate and a clear shift from production to consumption at 40 mM. No such effect was detected with NaCl supplementation.

Example 2

Adapting Cells to Sufficient Lactate Concentration

To investigate whether cell growth can recover in lactate supplemented media, an attempt to adapt the cells was explored. The Native Control cells were thawed and grown in conditions described in Table 1. Basal medium was the commercially available serum-free, chemically-defined Opti-CHO medium supplemented with 8 mM glutamine (Invitrogen, Carlsbad, Calif.). Adaptation to high lactate levels occurred by continuously passaging the cells in starting lactate levels ranging between 25 to 44 mM as measured by a Bioprofile 400. Ninety sequential passages over 9 months were performed in total to monitor stability and run parallel experiments. For the media formulation, the final lactate concentration chosen was 35 mM. The cells successfully adapted to this level of lactate supplementation will hereafter be referred to as "Lactate Adapted" cells.

A second control cell line was adapted in a similar fashion to basal medium supplemented with sodium chloride (NaCl) (Sigma, Lowell, Mass.) NaCl levels were chosen to match the osmolality of the Lactate Adapted conditions. This level was 410 mOsmo. The cells successfully adapted to this level of osmolality will hereafter be referred to as "Osmo Adapted" cells.

Specific net growth rates were measured per passage and plotted over time (FIG. 2A). Lactate Adapted cultures took approximately six weeks (11 passages) to double the net growth rate, thereby matching the growth rate of Native Control cells. A comparison of lactate concentrations in the basal medium formulation and initial lactate levels measured by the Bioprofile on day 0 are shown in FIG. 2B. The gradual increase of lactate to 35 mM in the medium formulation did not negatively impact cell growth.

The Osmo Adapted line was adapted in a similar fashion to NaCl supplementation. FIGS. 2C and 2D demonstrate comparable specific growth rates and very low death rates for both cell lines post adaptation, indicating a greater improvement in viable cell growth for Lactate Adapted cells. Both lines were continually passaged for six months and maintained tolerance and stability. The 11 passage cycles required to isolate Lactate Adapted cells is very reasonable compared to typical cell adaptation times seen historically (Birch et al., 1994, *Cytotechnology*, 15:11-16; Christie and Butler, 1999, *Biotechnol Bioeng*, 64:298-309; and Sinacore et al., 1996, *Biotechnol Bioeng*, 52:518-528).

The six week adaptation process and simplicity of implementation provide numerous advantages over other strategies devised to limit excessive lactic acid build-up.

Example 3

Metabolic Efficiency of Cells in Sufficient Lactate

In view of the mass action model, a lactate supplementation strategy may reduce process variability with respect to glucose metabolism. To determine if the sufficient lactate concentration identified in Example 1 altered the glucose metabolism of the cells, both lactate production and glucose consumption were measured.

Lactate Adapted cells were continuously passaged in medium containing 0 to 40 mM lactate. As illustrated in FIG. 3, specific lactic acid production rates decreased with increasing initial lactate concentration. Inoculating cultures between 35 to 40 mM lactate substantially reduced lactic acid production with zero net flux predicted to be slightly above 40 mM.

A wide distribution of lactic acid production for cultures batched without lactate can be observed in FIG. 3. As lactate additions increased, the distribution became tighter, minimizing process variability.

Lower lactic acid production ($q_{Lac}$) was also accompanied by a modest drop in specific glucose consumption ($q_{Gluc}$.) The amount of lactate produced per glucose consumed ($Y_{l/g}$) suggests a greater proportion of carbon was oxidized allowing a more efficient metabolic state to be reached (Table 2). All cultures were batched at similar glucose concentrations. With sufficient lactate supplementation, glucose need not be controlled at low levels to minimize lactic acid production.

TABLE 2

Average growth and metabolic rates of adapted cells.

| Cell-Line | $\mu_n$ ($p \approx 0.01$) (1/hr) | $q_{Lac}$ ($p < 0.001$) (μmol/$10^6$ cell-hr) | $q_{Gluc}$ ($p < 0.001$) (μmol/$10^6$ cell-hr) | $Y_{l/g}$ ($p < 0.001$) |
|---|---|---|---|---|
| Lactate Adapted | 0.025 ± 0.001 | 0.022 ± 0.018 | 0.054 ± 0.006 | 0.388 ± 0.344 |
| Osmo Adapted | 0.027 ± 0.002 | 0.112 ± 0.032 | 0.078 ± 0.012 | 1.411 ± 0.284 |

Inhibiting the pyruvate to lactate flux minimizes the amount of NAD$^+$ available for the continued oxidation of glucose (Lao and Toth, 1997, *Biotechnol Prog,* 13:688-691 and Lehninger, 1975, Principles of Biotechnology). The observed reduction in glucose consumption may partly be related to an altered redox state in the cytosol. Reduced glucose consumption rates delay glucose depletion.

Example 4

Lactate Adapted Cells Grown without Lactate Supplementation

A mechanism of mass action was further studied by culturing Lactate Adapted cells without lactate supplementation. While growth rates were unaffected by culture without exogenous lactate, Lactate Adapted cells reverted back to high glucose consumption and lactic acid production (FIG. 4). It is evident that Lactate Adapted cells conserve high glycolytic ability. These results indicate mass action behavior. More importantly, the results indicate that one can simply change lactate levels in the basal medium and control the balance between lactate consumption versus production.

Example 5

Cells in Sufficient Lactate Produce Less Ammonium

Since glucose and glutamine are complimentary substrates linked via the TCA cycle, a mass action balance may also alter ammonium ($NH_4^+$) production rates in cultures inoculated in lactate supplemented medium. Therefore, in order to test the affect of growing cells in the high lactate concentration, glutamine consumption and ammonium production were measured.

Reaction 2 below is a simplified pathway illustrating the interaction between glycolysis and glutaminolysis (Godia and Cairo, 2006, "Cell Metabolism," in Hu, W. S., Ozturk, S. S., 2006, *Cell Culture Technology for Pharmaceutical and Cell-Based Therapies.* Florida: CRC Press. pp. 89-92):

Reaction 2: Interaction between glycolysis and glutaminolysis

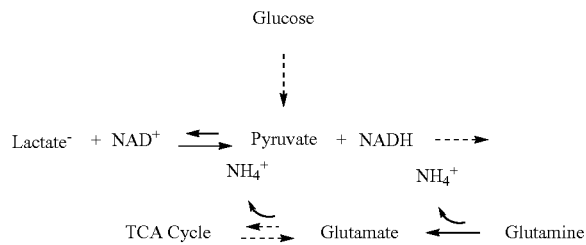

Lactate Adapted cells produced 40% less ammonium per cell than Osmo Adapted cells despite similar glutamine uptake rates (FIG. 5). Although similar affects were noted when feeding lactate to anti-apoptotic engineered CHO cells (Dorai et. al., 2009, *Biotechnol Bioeng,* 103(3):592-608), it is more common to see an increase in ammonium production following a drop in glucose consumption (Altamirano et al., 2000, *Biotechnol Prog,* 16:69-75 and Maranga and Goochee, 2006, *Biotechnol Bioeng,* 94:139-150). This behavior is often attributed to an increased dependency on glutamine for energy. The absence of this behavior in Lactate Adapted cells suggests the assimilation of lactate as an alternative energy substrate.

Similar specific glutamine consumption rates imply that the ammonium produced by the first deamidation of glutamine to glutamate is likely unaffected. Differences in glutamate deamidation, however, may partly be responsible for the lower ammonium levels. Changes in glutamate flux could contribute to growth inhibition prior to adaptation. These results demonstrate the unique ability to simultaneously minimize lactic acid and ammonium formation with a single change in medium formulation.

These observations indicate that highly concentrated medium formulations may be used without excessive nutrient consumption and waste metabolite accumulation.

Example 6

Effect of Lacate and Osmolality in Longer Term Cultures

In order to test how the adapted cells would perform over a longer duration typical of production cultures, the Lactate Adapted and Osmo Adapted cells were grown in shaker flasks for 12 days. Mean growth curves are shown in FIG. 6A. While both cell lines peaked at the same time, the Osmo Adapted cultures immediately entered the death phase characterized by a steep decline in viability. The Lactate Adapted culture maintained a longer stationary phase with a moderate decline in viability, allowing similar integrated viable cell density (FIG. 6A, insert). Differences in specific total and net growth rates were minor for the first 7 days of culture but markedly different after day 7 (FIG. 6B). Lactate Adapted cultures were characterized by a less significant drop in specific net growth and significantly lower death after glucose depletion. It is proposed that the lactate supplements provide additional nutrients whereas NaCl does not. The data suggest that some lactate may be effectively catabolyzed into biomass allowing the cells to rely less on glycolysis for energy needs.

Example 7

Lactate Supplement Improves pH Stability

The use of lactate supplementation as a means to improve pH stability was also investigated. For the same shaker flask cultures illustrated in FIGS. 6A and 6B, FIGS. 6C and 6D show the impact lactate supplementation had on residual lactate levels and pH trajectories. Up to day six, the lactate levels for the Osmo Adapted cells increased far more than for the Lactate Adapted cells (FIG. 6C). After day 6, both cultures entered a lactate consumption phase. During the initial growth phase of cultures, the pH trajectory for the Osmo Adapted cells dropped sharply, reaching pH 6.7 on day 5 (FIG. 6D). In contrast, the pH trajectory for the Lactate Adapted cells maintained a milder profile, remaining above pH 7.0 at all times. Both cultures exhibited an increase in pH during the lactate-consumption phase.

The metabolic redistribution caused by the exogenous lactate concentration improved pH stability and thus may be used to eliminate or reduce the need for base additions to control pH. Lactate supplementation can be used to control the metabolism of cells, as well as pH trajectories, by simply changing lactate levels and thus controlling the balance of lactate consumption versus production.

Example 8

10 Day Fed-Batch Culture of Lactate Adapted Cells

Growth inhibition by lactic acid is often contributed to excessive osmolality increases by base additions in pH-controlled bioreactors. This reduces the amount of nutrients that can be added without creating hyperosmotic stress. However, as demonstrated herein, cells cultured in a sufficient concentration of lactate have reduced lactic acid production and, therefore, require a decreased amount of base additions to control pH. As indicated in FIG. 6D, if such cultures were grown in larger bioreactors, equipped with automatic pH control, the base additions required to maintain pH at a proposed set-point of 7.0 would be reduced, as would also be the negative impact of hyperosmolality from those base additions. More nutrients can thus be added in a fed-batch system without excessive increases in osmolality, an important consideration in designing fed-batch processes that are often characterized by shifting lactate profiles and challenging pH control dynamics (Chu and Robinson, 2001, *Curr Opin Biotechnol*, 12:180-187; Godia and Cairo, 2006, "Cell Metabolism," in Hu, W. S., Ozturk, S. S., 2006, *Cell Culture Technology for Pharmaceutical and Cell-Based Therapies*. Florida: CRC Press. pp. 89-92; and Meier, 2005, "Cell culture scale-up: mixing, mass transfer, and use of appropriate scale-down models", *Biochemical engineering XIV*. Harrison Hot Springs, Canada).

In order to determine the effect of exogenous lactate on the osmolality of cell culture conditions, Lactate Adapted and Osmo Adapted cells were cultured in pH controlled fed-batch bioreactors as previously described. The osmolality of the basal medium was 330 mOsmo. The commercially available serum-free chemically-defined Efficient Feed B liquid medium kit (Invitrogen, Carlsbad, Calif.) was added to the cultures as feeds on days 2, 5 and 7. The first feed volume was 15% of the initial bioreactor working volume, while the second and third feeds were 10% of initial bioreactor working volume. Osmolality of the feed was 385 mOsmo. The initial bioreactor working volume was 1.6 liters.

Figure 7A:
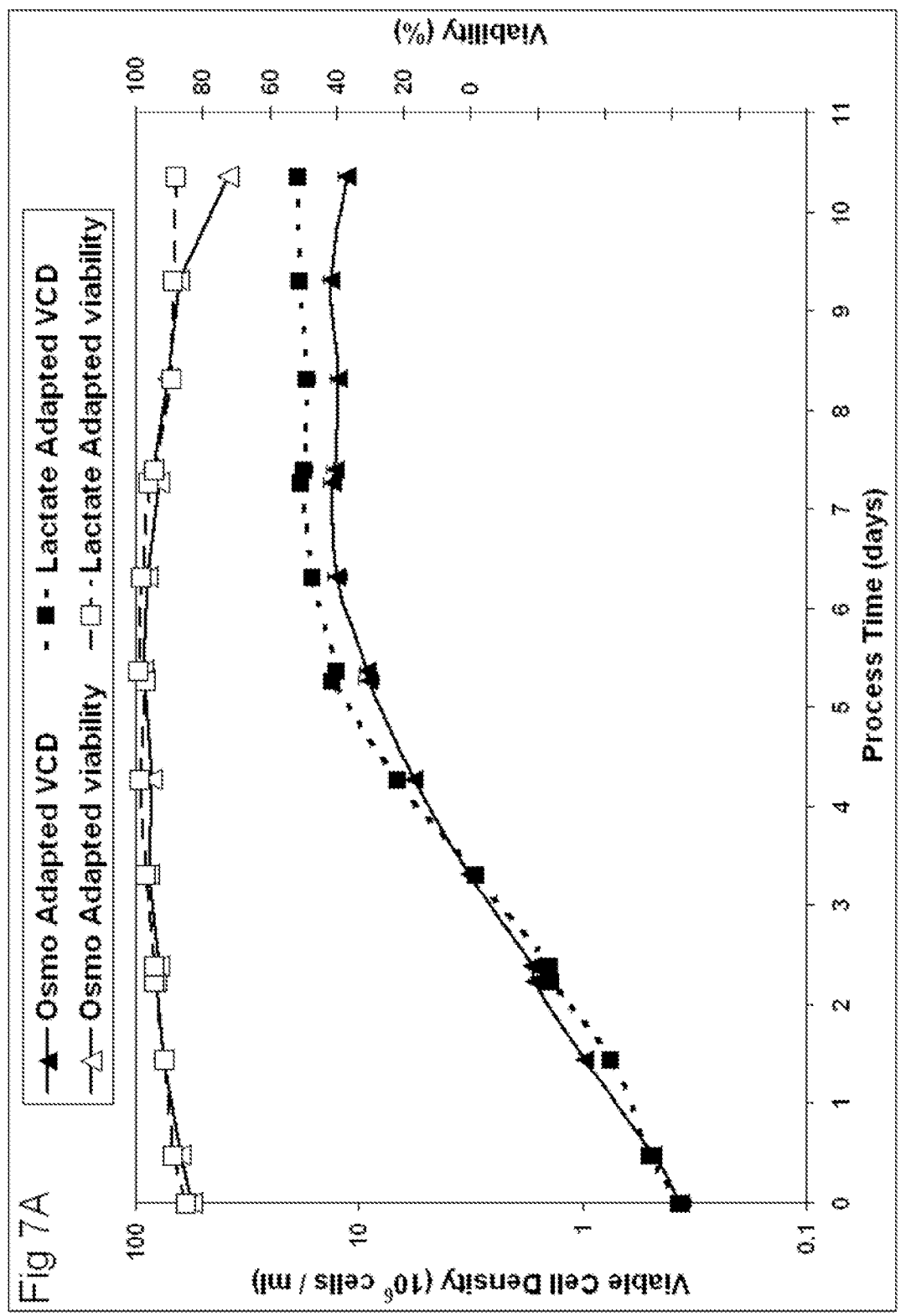
FIG. 7A is a line graph that shows the average viable cell density (VCD) and viability profiles of Osmo Adapted and Lactate Adapted cells under pH controlled, fed-batch conditions. Cultures were fed on days 2, 5 and 7.

For the first three days, Lactate Adapted and Osmo Adapted cells expressed similar growth rates under this feeding schedule (FIG. 7A). FIG. 7B plots the osmolality trajectories of both conditions. Osmolality of the Lactate Adapted culture remained steady and even decreased slightly over a period of 10 days. In contrast, lactic acid production in the Osmo Adapted culture surpassed the buffering capacity of the basal medium and the osmolality began to rise by day 4. Subsequently, the osmolality was higher and the net growth rate lower for the Osmo Adapted cells versus the Lactate Adapted cells.

The differences in base requirements are listed in Table 3. Base additions were reduced by over three fold in Lactate Adapted cultures. The distinct osmolality trajectories demonstrate that a lactate supplementation strategy does work in practice and more concentrated nutrient feeds could be used without excessive increases in osmolality. In fact, the slight decline in osmolality for the Lactate Adapted cells indicates that even more feeds could be added to such cultures without leading to excessive increases in osmolality.

TABLE 3

Amount of base added to the bioreactor to maintain pH.

| Cell Line | Base |
|---|---|
| Osmo Adapted | 160-165 ml |
| Lactate Adapted | 45-50 ml |

Example 9

High Cell Density Fed-Batch Culture of Lactate Adapted Cells

To investigate the impact of exogenous lactate on the performance of cultures receiving even higher levels of concentrated nutrient feeds, Lactate Adapted and Osmo Adapted cells were cultured in similarly-configured pH controlled fed-batch bioreactors with the following medium and feed schedule improvements.

Table 4 describes the concentrated nutrient feed solutions used for this experiment. For Feed Solutions 9.1 and 9.2, CD CHO AGT complete medium powder (Invitrogen, Carlsbad, Calif.) was added at levels of 12 to 24 g/L, respectively, to Efficient Feed B, purchased as a 1× liquid from Invitrogen (Carlsbad, Calif.). An additional 40 ml/liter of 200 mM glutamine was also added to Feed Solutions 9.1 and 9.2. The resulting glucose levels in Feed Solutions 9.1 and 9.2 were 21 g/L and 24 g/L, respectively. Two additional feed solutions, 9.3 and 9.4, were prepared and consisted of concentrated solutions of glutamine and glutamine plus glucose, respectively.

TABLE 4

Concentrated nutrient feed solutions.

| Feed Solution | Efficient Feed B | CD CHO AGT | Component Levels in Given Feed Solution Glutamine | Glucose | Measured (*) or theoretical (+) Osmolality |
|---|---|---|---|---|---|
| 9.1 | 1× | 12 g/L | 8 mM | 21 g/L | 540 mOsmo* |
| 9.2 | 1× | 24 g/L | 8 mM | 24 g/L | 700 mOsmo* |
| 9.3 | — | — | 200 mM | — | 200 mOsmo+ |
| 9.4 | — | — | 300 mM | 500 g/L | 3080 mOsmo+ |

The initial working volume of each culture was 1.6 liters. The osmolality of the basal medium was 315 mOsmo. Table 5 describes the feeding schedule of the solutions listed in Table 4. The feed volumes were based partly on maintaining a sufficient concentration of glucose. Every 24 hours the cultures were sampled, glucose was measured, and a sufficient volume of concentrated nutrient feeds were added to insure glucose levels would remain above 1 g/L over a 24 hour period. Glucose levels in the Osmo Adapted culture were lower than in the Lactate Adapted cultures, and were thus the determining factor for the feed volumes. Feeds continued until the entire bioreactor working volume of roughly 3 liters was used. The feeding schedule shown in Table 5 was used for both the Osmo Adapted and Lactate Adapted cultures.

TABLE 5

Concentrated nutrient feed schedule.

| Feed Solution | Day 3 | Day 4 | Day 5 | Day 6 | Day 7 | Day 8 | Day 9 |
|---|---|---|---|---|---|---|---|
| 9.1 | 80 ml | 80 ml | 160 ml | 160 ml | | | |
| 9.2 | | | | | 320 ml | 185 ml | 80 ml |
| 9.3 | | | 16 ml | 16 ml | 32 ml | | |
| 9.4 | | | | | | 20 ml | 20 ml |

The fed-batch growth and viability curves over the 15 day cultivation are shown in FIG. 8A. In comparison to the Osmo Adapted culture, the Lactate Adapted culture began to outperform after feeds were initiated. Lactate Adapted cultures achieved significantly improved viable cell densities, reaching as high as $35 \times 10^6$ cells/ml. In addition, the percentage of viable cells was also improved (FIG. 8A, right axis), allowing stationary growth to be maintained for an extended 15 days and integrated viable cell densities to nearly double (FIG. 8A, insert).

As shown in FIG. 8B, the pH levels for both cell culture conditions were well maintained near the set point value of 7.05. The amount of base required to maintain steady pH in each of the culture conditions is listed in Table 6. Approximately eight times more base was required to maintain pH in the Osmo Adapted cultures in comparison to the Lactate Adapted cultures. In addition, the Lactate Adapted cultures used similar amounts of base in both Example 8 and 9, demonstrating the ability to better predict base usage, even with a change in feeding schedules.

TABLE 6

Amount of base added to the bioreactor to maintain pH.

| Cell Line | Base |
|---|---|
| Osmo Adapted | 320-325 ml |
| Lactate Adapted | 40-45 ml | pH drift can also be partially contributed to respiratory carbon dioxide build up at high cell densities. As shown in FIG. 8C, similar bioreactor configurations allowed carbon dioxide levels produced by both cultures to be comparable over most of the course of the study. The carbon dioxide level in the Osmo Adapted cultures was somewhat higher toward the end, possibly due to much higher levels of sodium carbonate base added to those cultures.

As expected, the Lactate Adapted culture produced a much lower amount of lactic acid in comparison to the Osmo Adapted culture (FIG. 8D). Lactate levels continuously increased to nearly 100 mM in the Osmo Adapted culture and then entered a lactate consumption phase after day 9. In contrast, the Lactate Adapted culture started at a higher lactate concentration, produced minimal lactate, and entered a lactate consumption phase by day 6 to consume all the exogenous lactate provided. Approximately eight times less lactic acid was produced, which coincides with the eight fold reduction in base additions required to control pH.

Figure 8E:
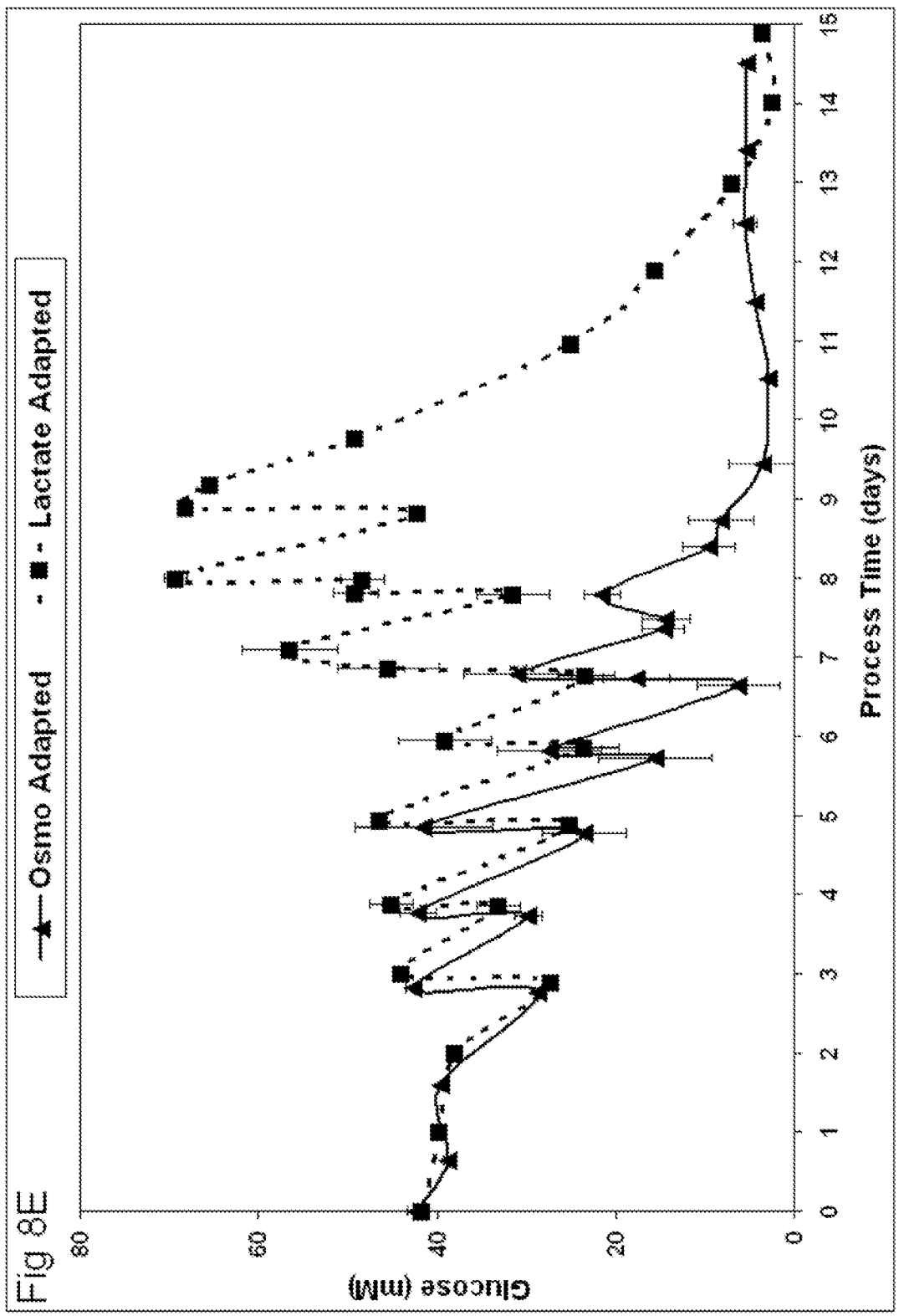
FIG. 8E is a line graph that shows corresponding time course profiles of residual glucose levels in Osmo Adapted and Lactate Adapted cultures.

It is interesting to note the glucose levels in the cultures after day 6 (FIG. 8E). It became increasingly difficult to maintain glucose levels in the Osmo Adapted culture while glucose levels in the Lactate Adapted culture continued to rise without impacting lactic acid production rates. By day 9, after the last feed was performed, glucose levels in the Osmo Adapted culture were below 5 mM, while 70 mM glucose was still available in Lactate Adapted cultures. These results suggest that glucose and lactate consumption supported cell maintenance and thus contributed to the extended life of the Lactate Adapted culture.

The impact lactate supplementation had on culture osmolality is clearly observed in FIG. 8F. Osmo Adapted cultures demonstrated excessive increases in osmolality that were, in contrast, avoided in the Lactate Adapted culture. Lactate Adapted osmolality remained below 400 mOsmo and started to decline after the last feed, partly due to consumption of lactate, and thus allowed more concentrated nutrient feeds to be added without excessive increases in osmolality. In contrast, osmolality in the Osmo Adapted culture exceeded 500 mOsmo and increased after the last feed.

These results demonstrate that concentrated nutrient feeds can be added to cells cultured in a sufficient concentration of lactate without leading to large increases in osmolality. In this manner, optimal amounts of nutrients can be added to cell cultures, including those grown in larger bioreactors, without creating hyperosmotic stress.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for producing a recombinant protein by a cell comprising adapting the cell to a sufficient concentration of exogenous lactate to reduce lactic acid production by the cell, thereby producing an adapted cell capable of growing in the sufficient concentration of exogenous lactate, and culturing the adapted cell in the sufficient concentration of exogenous lactate to reduce lactic acid production by the cell, wherein said adapting the cell occurs prior to said culturing the adapted cell and wherein the cell comprises a polynucleotide that encodes a recombinant protein, thereby producing the recombinant protein by culturing the lactate adapted cells.

2. The method according to claim 1, wherein said sufficient concentration of lactate is about 5 to about 100 mM lactate.

3. The method according to claim 2, wherein said sufficient concentration of lactate is about 20 to about 80 mM lactate.

4. The method according to claim 1, wherein lactate yield from glucose ($Y_{1/g}$) by the adapted cell is less than 0.3 moles lactate produced per mole glucose consumed.

5. The method according to claim 1, wherein said sufficient concentration of lactate reduces the specific lactic acid production rate of the adapted cell by at least 50%.

6. The method according to claim 1, wherein said exogenous lactate is one or more lactate salts or analogs selected from the group consisting of sodium lactate, potassium lactate, calcium lactate, zinc lactate, magnesium lactate, ammonium lactate, lactic acid, glycolate and 2-methyl-lactate.

7. The method according to claim 6, wherein said exogenous lactate is sodium lactate.

8. The method according to claim 1, wherein said culturing step comprises an initial cell concentration of about $0.3 \times 10^6$ to about $1.0 \times 10^6$ cells/ml.

9. The method according to claim 1, wherein said culturing step comprises adding exogenous lactate to the adapted cell more than one time.

10. The method according to claim 1, wherein said adapted cell is cultured with glucose at a concentration of about 1 to about 12 g/L.

11. The method according to claim 1, wherein said adapted cell produces less ammonium in the presence of the sufficient concentration of exogenous lactate than said adapted cell in the absence of the sufficient concentration of exogenous lactate.

12. The method according to claim 1, wherein said cell is a Chinese hamster ovary (CHO) cell.

13. The method according to claim 1, wherein said recombinant protein comprises an antibody, or a fragment thereof.

14. The method according to claim 1, wherein said culturing does not require an external pH control system to maintain optimum cell growth and viability.

15. The method according to claim 1, wherein said adapting comprises culturing said cell for about 4 to about 12 weeks with the sufficient concentration of exogenous lactate.

16. The method according to claim 15, wherein said adapting further comprises passaging said cell every 2 to 6 days.

\* \* \* \* \*